United States Patent [19]
Oaks et al.

[11] Patent Number: 5,585,450
[45] Date of Patent: Dec. 17, 1996

[54] OLIGOMERIZED CYCLOBUTARENE RESINS

[75] Inventors: Frank L. Oaks, San Carlos, Calif.; Eric S. Moyer, Midland, Mich.; Edward W. Rutter, Jr., Midland, Mich.; Robert F. Harris, Midland, Mich.

[73] Assignee: The Dow Chemical Company, Midland, Mich.

[21] Appl. No.: 465,666

[22] Filed: Jun. 5, 1995

Related U.S. Application Data

[60] Division of Ser. No. 290,197, Aug. 15, 1994, which is a continuation-in-part of Ser. No. 805,395, Dec. 10, 1991, abandoned.

[51] Int. Cl.$^6$ .................................................... C08F 130/08
[52] U.S. Cl. ........................................... 526/279; 526/284
[58] Field of Search ............................... 526/279, 284

[56] References Cited

U.S. PATENT DOCUMENTS

| | | |
|---|---|---|
| 2,852,379 | 9/1958 | Hepher et al. . |
| 2,940,853 | 6/1960 | Sagura et al. . |
| 4,106,943 | 8/1978 | Ikeda et al. . |
| 4,294,908 | 10/1981 | Harita et al. . |
| 4,540,763 | 9/1985 | Kirchhoff . |
| 4,564,576 | 1/1986 | Saigo et al. . |
| 4,565,767 | 1/1986 | Kataoka et al. . |
| 4,642,329 | 2/1987 | Kirchhoff et al. . |
| 4,730,030 | 3/1988 | Hahn et al. . |
| 4,743,399 | 5/1988 | Kirchhoff et al. . |
| 4,812,588 | 3/1989 | Schrock . |
| 4,831,172 | 5/1989 | Hahn et al. .............................. 556/419 |
| 5,041,600 | 8/1991 | Wong . |
| 5,156,656 | 10/1992 | Parker et al. . |

FOREIGN PATENT DOCUMENTS

| | | |
|---|---|---|
| 0140319 | 5/1985 | European Pat. Off. . |
| 0334381 | 9/1989 | European Pat. Off. . |
| 0527572 | 2/1993 | European Pat. Off. . |
| 2-330515 | 11/1990 | Japan . |

OTHER PUBLICATIONS

Chemical Abstract 13948t, vol. 74, 1971.
Chemical Abstract 103705m, vol. 75, 1971.
Specht, Donald P. et al., *Tetrahedron*, vol. 38, No. 9, pp. 1202–1211 (1982).
Johnson, R. W. et al., *IEEE Transactions on Components, Hybrids, and Manufacturing Technology*, vol. 13, No. 2, pp. 347–252, Jun. 1990.
Reche J. J. H., *IEEE Transactions on Components, Hybrids, and Manufacturing Technology*, vol. 13, No. 3, pp. 565–569, Sep. 1990.
Lai, J. H., CRC Press, Inc., Boca Raton, Florida, pp. 9–11 (1989).
Stokich, T. M. et al., *Mat. Res. Soc. Symp. Proc.*, vol. 227, pp. 103–114 (1991).
Bair, H. E. et al., *ANTEC*, pp. 1550–1553 (1991).
*Encyclopedia of Polymer Science and Engineering*, vol. 11, pp. 186–212, J. Wiley & Sons.
Research Disclosure 26808, Aug. 1986, p. 451.

*Primary Examiner*—Joseph L. Schofer
*Assistant Examiner*—Wu C. Cheng
*Attorney, Agent, or Firm*—Charles J. Enright

[57] ABSTRACT

An oligomerized cyclobutarene containing 80 weight percent or more of oligomers of a degree of polymerization of three or more.

10 Claims, No Drawings

OLIGOMERIZED CYCLOBUTARENE RESINS

CROSS REFERENCE TO RELATED APPLICATION

This is a divisional of application Ser. No. 08/290,197 filed Aug. 15, 1994, which is a continuation-in-part of U.S. application Ser. No. 805,395, filed on Dec. 10, 1991, now abandoned, which is incorporated herein by reference.

BACKGROUND OF THE INVENTION

This invention relates to photodefineable polymers and processes for preparing them.

Such polymers are used in passivation films, photoresists, as insulating layers in fabricating electrical devices and as protective films for semiconductor elements.

It would be desirable to have photodefineable polymers with a low dielectric constant, a low dissipation factor, low moisture uptake, high sensitivity, high contrast, high resolution, thermal stability, enhanced oxidative stability, resistance to chemicals and plasmas, good adhesion, low release of volatiles during cure, good processability and good planarization.

SUMMARY OF THE INVENTION

This invention, in one aspect, is a photodefineable, organic-soluble mixture comprising at least one cyclobutarene as its major component and at least one photosensitive agent in an amount sufficient to convert the mixture to an organic-insoluble solid upon exposing the mixture to photon radiation.

In a second aspect, this invention is the photo-cured organic-insoluble solid polymer resulting from photon irradiation of the photodefineable mixture. These photodefined polymers are useful in applications such as photoresists, etching masks, interlayer dielectrics, liquid crystal displays, and flat panel displays.

In a third aspect, the photodefineable mixture can be applied to a substrate, portions of the applied mixture are exposed to photon radiation and the substrate is then treated with an organic developing solvent to remove the ungelled portion of the mixture; this invention being the pattern-coated substrate resulting from this procedure having the photodefineable portion of the mixture adhered thereto.

In a fourth aspect, the photodefined composition of the second or third aspect is subjected to thermal curing. These photo/thermally cured polymers are useful in many applications; some of which include composites, laminates, membranes, films, electronics, coatings, and adhesives. The electronic applications include such areas as multichip modules and printed circuit boards.

In a fifth aspect the invention is a process for making a patterned solid polymer comprising the steps of coating a substrate with a mixture containing at least one cyclobutarene as its major component and at least one photosensitive agent, exposing a portion of the coating to photon radiation in an amount sufficient to convert that portion of the coating to an organic-insoluble solid, exposing the film to a solvent for the unexposed portion which is also a non solvent for the exposed portion to form a patterned solid polymer coating.

DETAILED DESCRIPTION OF THE INVENTION

The cyclobutarenes suitably employed as the major component in the photodefineable mixtures of this invention correspond to the formula $$B \left[ Ar \left\langle \begin{array}{c} C(R^2)_2 \\ | \\ C(R^2)_2 \end{array} \right\rangle_m \right]_n$$

wherein

B is a monovalent organic moiety, a direct bond, an n-valent bridging member comprising (1) a polyvalent inorganic moiety, or (2) a polyvalent organic moiety, or B is absent;

Ar is a polyvalent aromatic or heteroaromatic moiety, an ar-poly-yl, having three or more valences, provided that the two carbon atoms of the cyclobutane ring on the fused side are bonded to adjacent carbon atoms on the same aromatic ring of Ar;

n is an integer of 1 or more;

m is an integer of 1 or more; and $R^2$ is a monovalent moiety.

The synthesis and properties of these cyclobutarenes, as well as the terms used to describe them are found in U.S. Pat. Nos. 4,540,763; 4,724,260; 4,783,514; 4,812,588; 4,826,997; 4,999,449; 5,185,391;, all of which are incorporated herein by reference.

Monomers of the formulae or soluble polymers and copolymers thereof are preferred.

Soluble homopolymers of a monomer of the formula are most preferred.

The depictions of this most preferred monomer herein should not be construed to define any particular geometric isomer or spatial orientation about the ethenylene double bonds. Compositions made by the processes disclosed herein contain positional isomers about these double bonds as well as other compounds. This monomer will be hereinafter referred to as DVS bis BCB.

The most preferred organopolysiloxane-bridged bisbenzocyclobutene monomers can be prepared by methods disclosed in U.S. Pat. Nos. 4,812,588; 5,136,069; 5,138,081; and 5,264,646.

Following one of the disclosed procedures for making the most preferred cyclobutarene monomer, one will obtain a mixture containing as a major component divinyltetramethyldisiloxane-bis-benzocyclobutene monomer. This monomer mixture has a low viscosity. Preferably, this monomer is partially polymerized or B-staged prior to addition of a photosensitive agent.

Suitable photosensitive agents employable in this invention are those which have an absorption maximum near the wavelengths of the photon source being used and effect cyclobutarene photo-curing. When a photosensitizer is used in conjunction with a photosensitive agent, suitable photosensitive agents are those capable of accepting energy from the photosensitizer.

Preferred photosensitive agents include azides, bismaleimides, acrylates, acetylenes, isocyanates, conjugated aromatic ketones, and benzophenone-containing polymers.

The most preferred group of photosensitive agents is the azides. The azides employed in preparing the polymers of this invention correspond to the formula $$Q-(N_3)_x$$

wherein

Q is an x-valent organic moiety, and x is an integer of 1 or more.

Examples of suitable azides, as well as their synthesis and properties are described in "Azides and Nitrenes, Reactivity and Utility", Academic Press, 1984; "Azides and Amines from Grignard Reagents and Tosyl Azide," Smith et al , J. Org Chem., 34, 3430, (1969); *"Encyclopedia of Polymer Science and Engineering,"* 2nd Edition, Volume 11, 186–212; Yang et al., Proc. SPIE-Int. Soc. Opt. Eng., 469 (Adv. Resist Technol.), 117–26, 1984; Wolf et al., J. Electrochem. Soc., 131 (7), 1664–70, 1984; Tsunoda et al., Photographic Science and Engineering, 17, 390, ( 1973 ); *Journal of Photographic Science*, 29, 188, (1976); "Organic Compounds with Nitrogen-Nitrogen Bonds" Ronald Prez Co., New York, N.Y., 1966; Boyer et al., Chem. Rev., 54, 1, (1954); Japanese Patent Number J01279240-A, U.S. Pat. Nos. 4,565,767; 4,294,908; 4,354,976, and European Patent Applications 90300546.0, 84112698.0, 84300837.6, 83810156.6.

Preferred azides are aromatic bisazides some examples of which are represented by the following formulae:

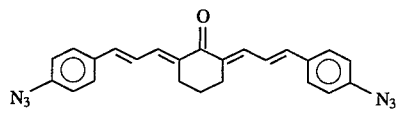

2,6-bis[3-(4-azidophenyl)-2-propenylidene] cyclohexanone

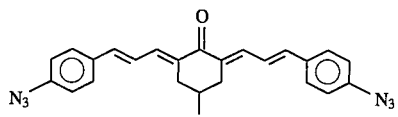

2,6-bis[3-(4-azidophenyl)-2-propenylidene]-4-methylcyclohexanone

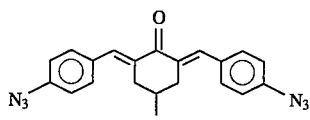

2,6-bis(4-azidobenzylidene)-4-methylcyclohexanone
(BAC-M)

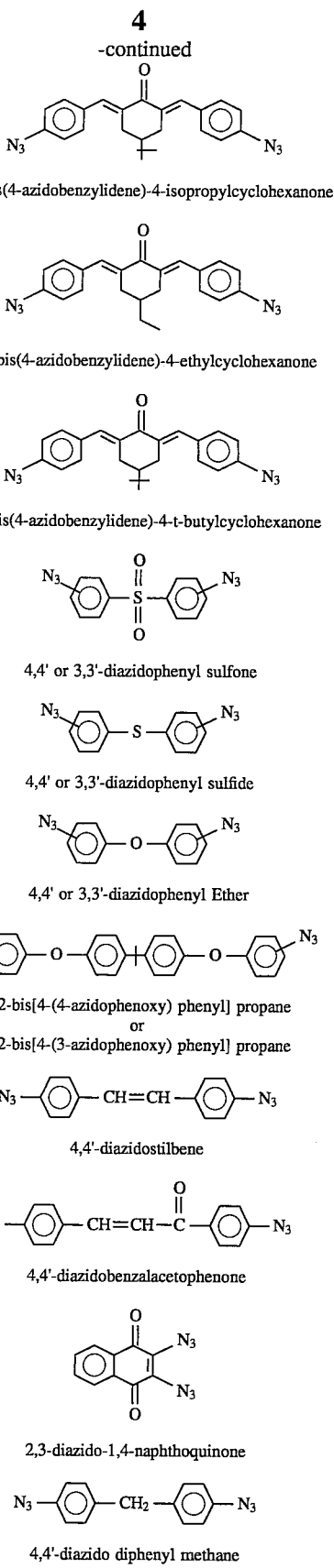

2,6-bis(4-azidobenzylidene)-4-isopropylcyclohexanone 2,6-bis(4-azidobenzylidene)-4-ethylcyclohexanone 2,6-bis(4-azidobenzylidene)-4-t-butylcyclohexanone 4,4' or 3,3'-diazidophenyl sulfone 4,4' or 3,3'-diazidophenyl sulfide 4,4' or 3,3'-diazidophenyl Ether 2,2-bis[4-(4-azidophenoxy) phenyl] propane
or
2,2-bis[4-(3-azidophenoxy) phenyl] propane 4,4'-diazidostilbene 4,4'-diazidobenzalacetophenone 2,3-diazido-1,4-naphthoquinone 4,4'-diazido diphenyl methane More preferred azides are highly conjugated aromatic bisazides such as BAC-M or 2,6-bis[3-(4-azidophenyl)-2-propenylidene]-4-methylcyclohexanone.

More preferred azides are highly conjugated aromatic bisazides.

The most preferred azide is determined by the wavelengths of the photon source employed. One chooses an azide which has an absorption maximum near the wavelengths of the photon source being used, or if a photosensitizer is being used in conjunction with the photosensitive agent one chooses an azide that will accept energy from the photosensitizer. Solubility of the azide in the system being used is also a consideration.

A suitable photosensitive agent for the DVS bis BCB resin of the invention is a 2,6-bis(4-azidobenzylidene)-4-alkylcyclohexanone such as 2,6-bis(4-azidobenzylidene)-4-methylcyclohexanone (hereinafter, BAC-M), 2,6-bis(4-azidobenzylidene)-3-methylcyclohexanone, 2,6-bis(4-azidobenzylidene)-4-ethylcyclohexanone, 2,6-bis(4-azidobenzylidene)-4-isopropylcyclohexanone, 2,6-bis(4-azidobenzylidene)-4-t-butylcyclohexanone or eutectic mixtures of these.

Another factor bearing on the choice of a bis azide is the thickness of the layer of DVS bis BCB resin to be patterned. BAC-M absorbs light at 365 nm. BAC-M is a good choice for thin layers such as 5 microns or less. In thicker layers such as 10 microns, one may wish to use BAC-M in conjunction with another bis azide that does not absorb at such a wavelength. Preferred second bis azides include 4,4' or 3,3'-diazidophenyl sulfone, 4,4' or 3,3'-diazidophenyl ether, 2,2-bis[4-(4-azidophenoxy)phenyl]propane or 2,2-bis[4-(3-azidophenoxy)phenyl]propane. More preferred bis azides for use in conjunction with BAC-M are 3,3'-diazidophenyl sulfone, 4,4'-diazidophenyl ether or 2,2-bis[4-(4-azidophenoxy)phenyl]propane. Most preferred is 3,3'-diazidophenyl sulfone.

One may wish to use these other bis azides, with less or no BAC-M for layers thicker than 12 microns. Preferred other bis azides include 3,3'-diazidophenyl sulfone, 4,4' or 3,3'-diazidophenyl sulfide, 4,4' or 3,3'-diazidophenyl ether, 2,2-bis[4-(4-azidophenoxy)phenyl]propane or 2,2-bis[4-(3-azidophenoxy)phenyl]propane. More preferred bis azides are 3,3'-diazidophenyl sulfone, 4,4'-diazidophenyl ether or 2,2-bis[4-(4-azidophenoxy)phenyl]propane. Most preferred is 3,3'-diazidophenyl sulfone.

The amounts of cyclobutarene and photosensitive agent employed in preparing the polymers of this invention can vary. Suitable amounts are those which contain one or more cyclobutarenes as the major component and provide a photodefineable mixture from which photodefined organic-insoluble polymers can be prepared. A suitable amount of photosensitive agent is that which provides sufficient curing in the photon-exposed portion of the mixture to render it insoluble in the developing solvent. A preferred weight percent range of photosensitive agent(s) is about 0.1 to about 20 based on the sum of the weights of the photosensitive agent and the cyclobutarene. A more preferred weight percent range of photosensitive agent is about 1 to about 6. The most preferred weight percent range of photosensitive agent is about 2 to about 4. A preferred weight percent range of the cyclobutarene is about 80 to about 99.9 based on the sum of the weights of the photosensitive agent and the cyclobutarene. A more preferred weight percent range of the cyclobutarene is about 94 to about 99. The most preferred weight percent range of the cyclobutarene is about 96 to about 98.

In addition to a cyclobutarene and a photosensitive agent, some embodiments of this invention contain one or more optional components which may be added to tailor the invention's characteristics.

An olefinic mono(cyclobutarene) may be added as an optional component to adjust the cured polymer's crosslinking density and/or improve its toughness. Olefinic mono(cyclobutarene) herein refers to a cyclobutarene moiety containing a carbon-carbon double bond. Suitable olefinic mono(cyclobutarene)s are represented by the formula

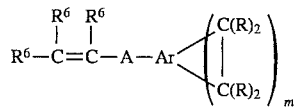

wherein

Ar is a polyvalent aromatic moiety, an ar-poly-yl, having three or more valences, provided that the two carbon atoms on the fused side of the cyclobutane ring are bonded to adjacent carbon atoms on the same aromatic ring of Ar;

A is a covalent bond or a divalent organic or inorganic moiety;

m is an integer of at least 1;

R is a monovalent moiety;

each $R^6$ is individually hydrogen or an alkyl moiety.

The synthesis and properties of these internal olefinic mono(cyclobutarene)s are described in U.S. Pat. No. 4,724,260.

An antioxidant may be added to increase the formulation's oxidative stability during processing as well as in the cured resin. Antioxidants of the phenol-, sulfide-, phosphite-, and amine type may be employed in this invention. Hindered amines are the preferred antioxidants. Hindered amines with aliphatic and aromatic moieties are more preferred antioxidants. The most preferred antioxidant is polymerized 1,2-dihydro-2,2,4-trimethylquinoline, CAS registry number 26780-96-1.

This antioxidant is available as an oligomer of the formula

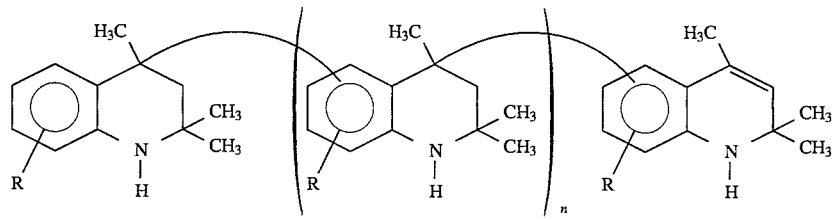

wherein R is hydrogen, an electron withdrawing or electron donating group and n is 0–6. Preferably R is hydrogen, but it also can be any substituent that does not interfere with the antioxidant activity of the compound.

2,2,4-Trimethyl-1,2-dihydroquinoline, wherein R is hydrogen, is available as AgeRite® MA from R. T. Vanderbilt as an oligomer with a degree of polymerization of about 3 or 4 (n is about 1 or 2).

Preferably, the optional antioxidant is employed at a weight percent range of less than 8, more preferably at a weight percent range of less than 7, and most preferably at 0.001 to 6 weight percent.

A photosensitizer may be added to increase the photosensitive agent's photosensitivity. The synthesis and properties of suitable optional sensitizers are disclosed in Specht et al., Tetrahedron, Vol. 38, No. 9, pp. 1203–1211, (1982); Tsunoda et al., Photographic Science and Engineering, 17, 390, (1973); U.S. Pat. No. 4,268,603; and European Patent Application 90300546.0. Suitable photosensitizers are those whose absorption maximum is near the wavelengths of the photon source employed. Preferred photosensitizers are represented by the following formulae:

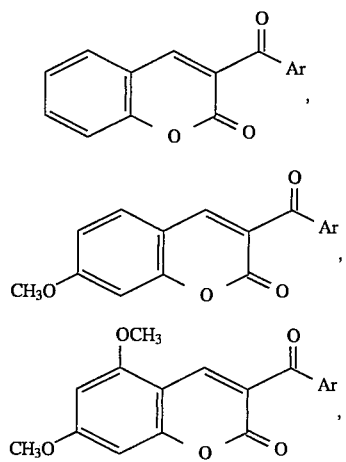

where Ar is represented by the following formulae:

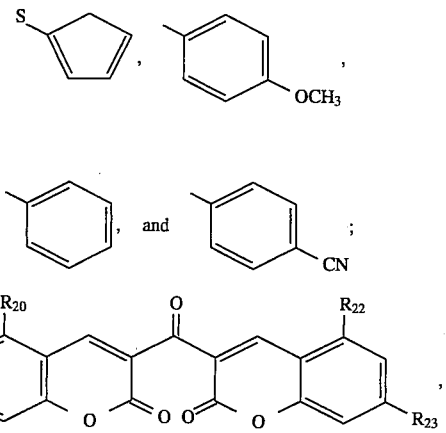

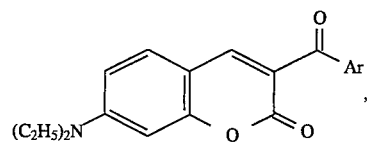

where $R^{20}$, $R^{21}$, $R^{22}$, $R^{23}$ are separately and independantly H, $OCH_3$, and $-N(C_2H_5)_2$;

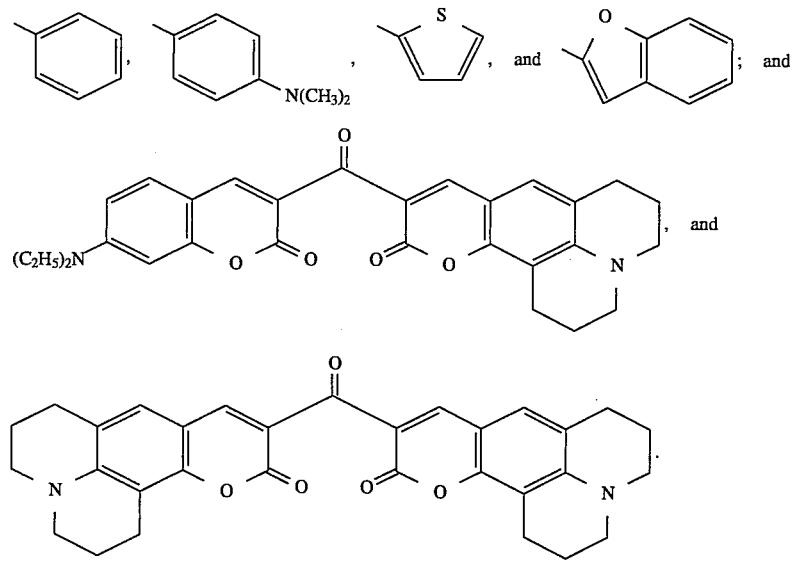

where Ar is represented by the following formulae:

More preferred photosensitizers are represented by the following formulae:

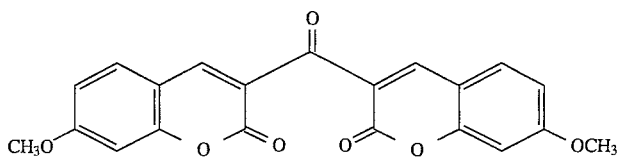

3,3'-carbonyl bis (7-methoxycoumarin)

and

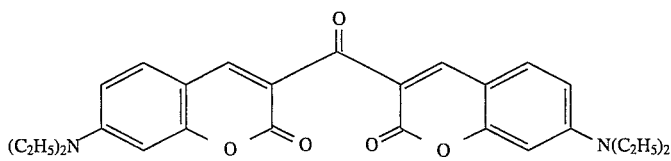

3,3'-carbonyl bis (7-diethylaminocoumarin).

In some applications, the photosensitive agent may act as a photosensitizer. For example, BAC-M may act as a photosensitizer for the diphenyl azides such as 4,4' or 3,3'-diazidophenyl sulfone, 4,4' or 3,3'-diazidophenyl sulfide, 2,2-bis[4-(4-azidophenoxy)phenyl]propane or 2,2-bis[4-(3-azidophenoxy)phenyl]propane or 4,4' or 3,3'-diazidophenyl ether.

Preferably, the optional photosensitizer is employed at a weight percent range of less than about more preferably at a weight percent range of less than about 3, and most preferably at about 0.001 to about 2 weight percent.

The cyclobutarene-containing portion of the formulation and any optional components may be oligomerized or B-staged prior to use to improve handling, processing, and performance characteristics. Preferably, the cyclobutarene is oligomerized without any photosensitive agent or other optional components present. The molecular weight of a resin directly impacts its performance in a photosensitive system. It is most preferred to have the highest molecular weight possible while maintaining a high solubility level. It is further desirable to have low polydispersity (Mw/Mn; where Mw is the weight-average molecular weight and Mn is the number-average molecular weight) so that the soluble oligomers are easily converted into an insoluble gel when exposed to a photon source. This will result in the maximum solubility difference between the exposed and unexposed areas of the polymer film covering the wafer or substrate. Mw can be controlled by the extent of conversion during oligomerization or B-staging. With the most preferred cyclobutarene, divinyltetramethyldisiloxane bisbenzocyclobutane, represented by the formula

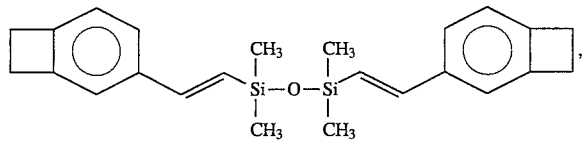

the gel point occurs while a significant portion of monomer and low molecular weight oligomers are present due to the complex nature of the linking group in this poly(cyclobutarene). The extent of conversion also affects the molecular weight distribution.

The average molecular weight and molecular weight distribution may also be altered by selectively removing some oligomeric mixture components. A wider range of oligomer molecular weights results in a wider range of oligomer solubilities after photo-curing. The lower molecular weight materials remain soluble after photocuring, thus it is desirable to remove them from the formulation prior to coating it on a substrate to minimize losses upon solvent development. The lower molecular weight materials may also be removed from the oligomerized cyclobutarene prior to adding a photosensitizer or other optional components. Preferably at least 80 weight percent of the cyclobutarene monomer is removed prior to coating the solution on a substrate. More preferably at least 80 weight percent of the cyclobutarene monomer and at least 50 weight percent of the cyclobutarene dimer is removed prior to coating the solution on a substrate. Even more preferably at least 80 weight percent of the cyclobutarene monomer and dimer is removed prior to coating. Most preferably at least 90 weight percent of the cyclobutarene monomer and dimer and at least 50 weight percent of the cyclobutarene trimer are removed.

The preferred oligomer may contain 80 weight percent or more of oligomers of a degree of polymerization of three or more. The more preferred oligomer may contain 90 weight percent or more of oligomers of a degree of polymerization of three or more. The most preferred oligomer may contain 95 weight percent or more of oligomers of a degree of polymerization of three or more. By a degree of polymerization of three or more is meant species of the molecular weight of trimers and higher.

One may determine the percentage of monomer, dimer and trimer in the oligomerized cyclobutarene by gel permeation chromatography (GPC). The weight percentage of monomer, dimer and trimer are approximately equal to the peak areas of the GPC trace. They are not exact because detection is by refractive index and the response factors for the monomer and dimer may vary somewhat from that of the oligomer. The approximation may be used and is used in the data in this specification. For more accurate determinations, the response factors for the monomer and dimer should be determined.

A preferred cyclobutarene oligomer may contain 80 weight percent or more of oligomers of a molecular weight of 1,000 or more as determined from peak area percent by GPC, using a refractive index detector, uncorrected for response factors and as measured against polystyrene standards. A more preferred cyclobutarene oligomer may contain 90 weight percent or more as determined from peak area percent of oligomers of a molecular weight of 1,000 or more, similarly determined. A most preferred cyclobutarene oligomer may contain 95 weight percent or more of oligomers of a molecular weight of 1,000 or more, similarly determined.

Various methods may be used to obtain the preferred molecular weight distribution of the cyclobutarene oligomer. The desired cyclobutarene monomer may be oligomerized or B-staged neat by heating. Then the lower molecular weight fractions may be removed by extraction in a nonsolvent for the higher molecular weight species. For example, one may dissolve the cyclobutarene oligomer in a miscible solvent and then mix it with a nonsolvent to precipitate out the higher molecular weight species. For the most preferred monomer, DVS bis BCB, mesitylene may be used as the miscible solvent and an alcohol such as t-amyl alcohol may be used as the precipitating solvent.

One means of effecting this removal is alcoholic precipitation, as exemplified in Example 16. Other techniques commonly used to separate the fractions of a polymer mixture may also be employed here, such as chromatography and solvent extraction, including supercritical solvent extraction.

B-staging of benzocyclobutanes is described in U.S. Pat. No. 4,642,329, which is incorporated herein by reference. When neat B-staging is complete, a solvent, sometimes called a casting solvent, is used to dissolve the B-staged material and thus may be used to facilitate its removal from the B-staging apparatus. Hydrocarbons are suitable solvents for most oligomeric cyclobutarene-containing systems. Preferred solvents for most oligomeric cyclobutarene-containing systems include xylene and mesitylene. The most preferred solvent is mesitylene. B-staging may also be performed in solution.

The cyclobutarene monomer may be partially polymerized in contact with a solvent. One polymerizes the monomer under conditions that yield a partially polymerized resin that will yield acceptable performance when used as a photodefineable resin in thin films. Acceptable performance includes retention of integrity such as absence of crazing. It also includes adequate film retention upon curing. Crazing is the formation of fractures or wrinkling in the thin film of the cyclobutarene resin as it is coated onto a substrate, as it is prebaked prior to photo-curing or when it is exposed to a development solvent. The fractures and wrinkling result in nonuniform thickness of the resin film. Film retention is the ratio of the thickness of the finally developed and cured film to the thickness of the initial film after being spun on and solvent removal usually designated in percent.

One may achieve acceptable resins, preferably, by controlling the initial concentration of cyclobutarene monomer in the solvent in the partial polymerization process. Preferably, for the most preferred DVS bis BCB monomer, the initial concentration is between 12 and 32 weight percent monomer based on the total weight of monomer and solvent. If the initial concentration is less than about 12 weight percent, the film formed from the partially polymerized resin has a tendency to craze upon evaporation of the solvent, upon solvent development of the film or during plasma cleaning of the cured film. If the initial concentration of the monomer is more than about 32 weight percent film retentions tend to be less than 50 percent.

The more preferable film properties may be obtained by using preferred initial DVS bis BCB monomer concentrations. Preferably, the initial DVS bis BCB monomer concentration is from about 17 percent to about 30 percent. More preferably, the initial DVS bis BCB monomer concentration is from about 20 to about 25 percent. Most preferably, the initial DVS bis BCB monomer concentration is 25 percent plus or minus 1 percent. The effect of initial DVS bis BCB monomer concentration, while a critical parameter, is not a step function. The changes in the final film properties are a smooth function of the initial monomer concentration under identical photo processing conditions.

One may carry out the partial polymerization process in a solvent that dissolves both the DVS bis BCB monomer and the partially polymerized DVS bis BCB resin at the reaction or polymerization temperature or one may carry out the partial polymerization process in a solvent that dissolves the DVS bis BCB monomer but not the desired partially polymerized DVS bis BCB resin at the reaction or polymerization temperature or one may carry out the partial polymerization process in a solvent that dissolves the DVS bis BCB monomer and the partially polymerized DVS bis BCB resin at the reaction or polymerization temperature but not the desired partially polymerized DVS bis BCB resin at lower temperatures. Suitable solvents depend on which process one wishes to use.

Solvents which dissolve the partially polymerized DVS bis BCB resin are hydrocarbons and the like. Aliphatic hydrocarbons such as hexane, Isopar G®, Stoddard solvent and the like; aromatic hydrocarbons such as toluene, xylenes and mesitylene are exemplary. More preferred solvents include aromatic hydrocarbons such as toluene, xylenes and mesitylene. Mesitylene is most preferred because it is also the formulation solvent. Another more preferred group is hydrocarbons which have normal boiling points at or below 165° C., so that the solvent may be easily removed from the resin by distillation and replaced by the formulation solvent.

Solvents from which the partially polymerized DVS bis BCB resin will precipitate include alcohols. $C_3$–$C_6$ alcohols are preferred with t-amyl alcohol and n-butanol being most preferred.

Preferably, the solvent and DVS bis BCB monomer are free of ions which would effect the dielectric properties of the final fully cured film. Exemplary ions excluded are metal ions such as alkali metal and transition metal ions, and anions such as halides, sulfates and nitrates.

One may carry out the partial polymerization at a temperature that is effective to polymerize the DVS bis BCB monomer. Suitable temperatures include from about 125° C. to about 300° C. Preferred temperatures include from about 140° C. to about 250° C. More preferred temperatures include from about 140° C. to about 200° C. If the polymerization temperature is higher than the boiling point of the solvent a pressure vessel may be used. At lower temperatures, the polymerization proceeds more slowly. At higher temperatures the degree of polymerization is more difficult to control.

One may carry out the partial polymerization for a time determined to provide a partially polymerized resin that provides the desired finally cured film properties. One may carry out the polymerization for a period of time sufficient to obtain an Mw of from about 20,000 to about 170,000. Preferably, one may carry out the polymerization for a period of time sufficient to obtain an Mw of from about 90,000 to about 170,000. Most preferably, one polymerizes the DVS bis BCB monomer to obtain a DVS bis BCB resin with an Mw of 140,000 plus or minus 10,000 g/mol.

Mw is the weight average molecular weight. Mn is the number average molecular weight. The ratio, Mw/Mn, is called the polydispersity of the resin. Molecular weights described in this application are apparent molecular weights. They are determined by size exclusion chromatography (SEC) using narrow molecular weight range linear atactic polystyrene polymers as standards. The polymers made in the processes described herein contain a relatively wider molecular weight range. Also, the monomer is tetrafunctional and may give rise to branched polymers.

The initial concentration of monomer affects the rate of reaction. The higher the initial concentration of monomer, the less time it takes to achieve a given Mw.

Preferably, one should not polymerize the DVS bis BCB resin beyond its gel point. Beyond its gel point, the resin is insoluble in aromatic solvents such as mesitylene. Time varies depending on the polymerization temperature. The higher the temperature, the less time is needed to obtain a given molecular weight.

Preferably, oxygen is excluded from the polymerization reaction. A concentration of less than 100 ppm oxygen in the atmosphere in contact with the reaction is suggested.

Some systems require a cosolvent to solubilize the photosensitive agent when it is present at higher concentrations. When the photosensitive agent is an azide, suitable cosolvents include ethers, glycol ethers, ketones, and esters. Preferred cosolvents are 2-methoxyethanol, 2-ethoxyethanol, 2-methoxyethylether, cyclopentanone and 2-ethoxyethylether. The most preferred cosolvents are cyclopentanone and 2-ethoxyethylether.

The photosensitive agent can be dissolved in the partially polymerized cyclobutarene resin/solvent system by conventional means such as agitation, sonication and heating. All manipulations of the cyclobutarene resin/photosensitive agent mixture are preferably performed in a darkened environment to prevent premature initiation of the photosensitive reaction by photon radiation. One means of providing a suitable environment is by using working space equipped with amber filtered (yellow) lights which filter out wavelengths of less than 500 nm.

Thin films of the cyclobutarene resin-containing formulation may be applied to substrates without the use of an adhesion promoter. When desirable, an optional adhesion promoter is formulated as a spray- or spin-on solution which is applied immediately before applying the cyclobutarene resin-containing formulation. Alternatively, the adhesion promoter is added to the cyclobutarene resin/photocrosslinking agent formulation.

The adhesion promoter is designed such that one end of the molecule either covalently attaches or adsorbs to the metal, metal oxide, or ceramic substrate surface, while the second end of the molecule reacts with the cyclobutarene resin polymer matrix. Suitable adhesion promoters include trialkoxyvinylsilanes and trialkoxyvinylsilyl benzocyclobutanes. The preparation and properties of trialkoxyvinylsilyl benzocyclobutanes are described in U.S. Pat. Nos. 4,831,172 and 5,002,808, which are incorporated herein by reference.

More preferred adhesion promoters include 3-aminopropyltriethoxysilane (3-APS), 3-methacryloxypropyl trimethoxysilane (MOPS)(CAS-02530-85-0), trimethoxyvinylsilane, triethoxyvinylsilane (TEVS), trimethoxyvinylsilyl benzocyclobutanes, and triethoxyvinylsilyl benzocyclobutanes. The most preferred adhesion promoter is 3-aminopropyltriethoxysilane (3-APS).

Suitable substrates are comprised of silicon, alumina, ceramic materials such as aluminum nitride, glasses, co-fired ceramics, copper sheet, printed circuit boards, polycrystalline diamond films, GaAs i.e., XIII–XV semiconductors, silicon nitride films, glass ceramic and high temperature polymer films such as polyimides and polybenzazoles. More preferred substrates are comprised of alumina and silicon. The most preferred substrate is silicon.

The cyclobutarene resin-containing formulations are applied from solutions containing 3 to 70 weight percent solids. The solids content and molecular weight of the cyclobutarene resin-containing formulation determine the viscosity of the spray- or spin-on solution. Spin-time and speed are used to control film quality and thickness at a particular formulation viscosity. Details of substrate coating with benzocyclobutane films can be found in the *Journal of Electronic Materials*, Vol. 19, No. 12, 1990, which is incorporated herein by reference.

In a preferred process wherein the DVS bis BCB resin formulation has a viscosity of 1100±50 cSt at 25° C., one may spin-coat the DVS bis BCB resin formulation at 68° F. to 70° F. at a relative humidity of 45 to 55 percent with a spread time of ten seconds at 500 rpm and a spin of 30 seconds at 2800 rpm. This generally yields a coating of 10 to 12 microns thick. A stream of xylene may be directed at the back of the substrate being coated to avoid dried resin (cotton candy) from adhering to the edges of the substrate.

The majority of the casting solvent is removed during the spin-coating process. A softbake cycle may be required to remove residual solvent. The softbake also relaxes stress resulting from the flow of the polymer film, increases the film's adhesion to the substrate, and hardens the film for more convenient handling during processing; for example, to prevent adhesion to a mask when printing in a hard contact mode.

The softbake may be performed in a convection oven, belt oven or on a hot plate. A preferred softbake temperature is one sufficient to remove residual solvent, provide stress relaxation which requires a temperature above the polymer's glass transition temperature, but low enough to avoid oxidizing or thermal curing of the resin or undesired reactions of the formulation additives and which allows the resin to flow sufficiently to promote planarization. The preferred softbake temperature will vary depending in part on the components of the cyclobutarene resin-containing formulation. A preferred softbake temperature for the most preferred DVS bis BCB resin ranges from 70° C. to 120° C. The most preferred softbake temperature is 75° C. The softbake is time temperature dependent. The higher the temperature, the less time is needed to softbake. One minute on a hot plate at 120° C. may achieve the same result as 20 to 30 minutes in an oven at 80° C. When using BAC-M it is preferred to softbake at 75° C. for 20 minutes because of its thermal instability.

A preferred softbake time is one sufficient to remove residual solvent, provide stress relaxation, but short enough to avoid oxidizing or thermal reaction of the resin components. The preferred softbake time will vary depending in part on the components of the cyclobutarene resin-containing formulation. A preferred softbake time for the most preferred DVS bis BCB resin ranges from 15 seconds to 60 minutes. The most preferred softbake time range depends on balancing desired performance results with maximizing throughput, may vary from 15 seconds to 30 minutes. To maximize throughput, the minimum time would be optimal.

Suitable softbake atmospheres include a vacuum, solvent vapor, air, nitrogen, argon, and helium. Nitrogen is the most preferred atmosphere. Oxygen is to be avoided.

Exposure time is dependent upon the photon source being used. Selective removal of various components of a high pressure mercury photon source may provide superior film performance. Suitable photon sources include those for which a suitable photo-sensitive agent exists that can absorb that photon source's wavelengths of energy. Preferred photon sources include visible light, ultraviolet light, X-rays, and electron beams. More preferred photon sources include ultraviolet and visible light. The most preferred photon source is a super high pressure mercury arc. The dose varies depending on the film thickness and the type of photosensitive agent used. For a 10 micron thick film, suitable dose at the I-line (365 nm) is 150 to 600 mJ/cm$^2$.

One may pattern the light striking the cyclobutarene resin formulation film by passing it through a mask in projection, proximity or soft contact mode in a conventional manner.

Following photon exposure, a softbake cycle may be employed. This cycle increases the reaction rate of long-lived photochemically generated intermediates. These intermediates have increased mobility during this cycle and thus may migrate and find a reactant species.

An alternative means of increasing the mobility of these reactive intermediates is heating during photon exposure. Such a procedure may increase the photo-sensitive agent's sensitivity.

Once photon exposure is complete, the film is solvent developed. Solvent development comprises the use of a solvent in which photo-exposed resin is only slightly soluble and the nonphoto-exposed resin is soluble to dissolve the nonphoto-exposed resin. The dissolved resin is then removed.

Suitable developing solvents are those which selectively dissolve the nonphoton-exposed film component while minimizing swelling of the photon-exposed film. Suitable solvents for unexposed cyclobutarene resin films include hydrocarbons such as Stoddard solvent, xylene, mesitylene, toluene, cyclohexane, decalin, dicyclohexyl or alkyl substituted benzenes such as t-amyl benzene, phenyl heptane, phenyl nonane, 1,4-diisopropyl benzene, or blends of hydrocarbons such as Aromatic 150 with Isopar L; esters such as ethyl myristate, methyl myristate, methyl laurate, ethyl undecanoate, ethyl-cinnamate, $C_5$–$C_{12}$ butyric esters such as ethyl butyrate and n-butyl n-butyrate; ethers such as pentyl, hexyl or octyl ether, 2-methoxyethyl ether (diglyme), 1,2-dimethoxybenzene, 1,3-dimethoxybenzene, dipropylene glycol dimethyl ether (Proglyde™ DMM solvent), or formulations of Proglyde™ DMM with Isopar® L (manufactured by Exxon, a blend of synthetic isoparaffinic hydrocarbons with a flashpoint of 147° F. consisting mainly of branched-saturated hydrocarbons with the majority of the distribution comprised of $C_{11}$ and $C_{12}$ hydrocarbons); Norpar® 12 (manufactured by Exxon, a paraffinic solvent blend consisting of straight-chain saturated hydrocarbons from $C_{10}$ up to $C_{14}$ and having a flashpoint of 151° F.); Norpar® 13 (manufactured by Exxon, a paraffinic solvent blend of straight-chain saturated hydrocarbons with a flashpoint of 203° F. and is similar to Norpar 12 except that the distribution has an overall higher average molecular weight); Dowanol™ TPM, Dowanol™ DPMA, Dowanol DPM or lactate esters such as butyl lactate. Other suitable solvents include N-methyl pyrrolidone (NMP), mixtures of NMP and 2-hydroxyethyl 2-pyrrolidone and a Stoddard/methanol mixture. Stoddard solvent as used herein is defined at page 1095, *"Hawley's Condensed Chemical Dictionary,"* 11th Edition, Van Nostrand Reinhold Company, New York, 1987.

The most preferred solvents for DVS bis BCB resin film systems are Stoddard solvent and formulations of Proglyde™ DMM dipropylene glycol dimethyl ether with hydrocarbons such as Isopar L or Norpar 12. Stoddard solvent gives better film retentions but is slow to dissolve the unexposed DVS bis BCB resin and has a low flash point. Proglyde™ DMM dipropylene glycol dimethyl ether gives lower film retentions but has a higher flash point and may be less toxic and teratogenic than, for example, diglyme. n-Butyl n-butyrate is a good choice for films less than 8 microns thick, but tends to cause crazing in thicker films. The choice of development solvent will to some extent be governed by the users choices between these attributes.

Preferred solvent development methods include spray, puddle or immersion techniques. Spray development is a preferred technique due to its amenability to large scale production. One preferred technique is puddling solvent on the wafer, allowing it to penetrate for a period of time which can be determined by experiment. Then the wafer is rinsed in the development solvent, the unexposed resin is dissolved, spun at a high speed to remove the solvent and solvent penetrated film. Preferred development methods may depend on the solvent. Diglyme is preferably puddled.

For the preferred formulation for a 10 micron thick film, one may puddle Stoddard's solvent at 68° F. for 2 minutes and then rinse for 20 seconds while spinning at 500 rpm and then spun dry at 4,000 rpm for thirty seconds.

One may use the most preferred DVS bis BCB resin made from DVS bis BCB monomer made using the exemplified monomer synthesis method, which is then solvent B-staged using the exemplified solvent B-staging procedure, with an initial concentration of 25 percent solids, to achieve an Mw of from about 140,000 to about 150,000. One may make coatings on the order of 5 to 7 microns thick using such a resin formulated with 3 weight percent BAC-M and 1 percent AgeRite® MA based on the DVS bis BCB resin. This is then diluted with additional mesitylene to a viscosity of 350±17 cSt at 25° C. (about 40 percent DVS bis BCB resin). One may make coatings on the order of 8 to 10 microns thick using such a resin formulated with 2 weight percent BAC-M, 0.75 weight percent 3,3'-diazidophenyl sulfone and 0.75 weight percent AgeRite® MA based on the DVS bis BCB resin. This is then brought to a viscosity of 1100±50 cSt at 25° C. with mesitylene (about 47 percent DVS bis BCB resin). One may make coatings on the order of 20 microns or more thick using such a resin formulated with 1 weight percent BAC-M, 0.9 weight percent 3,3'-diazidophenyl sulfone and either 0.75 or 1 weight percent AgeRite® MA.

To make 20 plus micron thick films, the spin speed must be lowered to, for example, 850 rpm for low viscosity solutions or one may increase the viscosity and spin at higher speeds. In any of these options, portions of the resin are photo-cured with 365 nm wavelength light for 600 to 1000 mJ/cm$^2$. A Proglyde™ DMM development solvent is puddled on the wafer for at least 90 seconds before being spun off. For the 5 micron coating, either Stoddard solvent or n-butyl n-butyrate is an effective solvent. For the 10 and 20 micron coatings, Stoddard solvent is preferred.

The solvent developed film may be post-baked to remove solvent. The post-bake may include elevation of the temperature to 120° C. to 140° C. for 0.5 to 2 minutes. Preferably, the 10 micron film may be post-baked on a hot plate in air at 100° C. for 1 minute.

At this point in the process, for example, after passing optical inspection, the patterned thin film may have additional microcircuitry and photodefined dielectric layers applied to it or it can be further thermally cured.

Procedures for preparing multilayer interconnect units or multichip modules are disclosed in the following references which are herein incorporated by reference: J. J. Reche, "Fabrication of High Density Multichip Modules," *IEEE/CMT 1989 IEMT Symposium*, p. 104; T. Tessier et al., "Process Considerations in Fabricating Thin Film MCM's," *IEPS 1989* p 294; S. F. Hahn et al., "The Fabrication and Properties of Thermoset Films Derived from Bisbenzocyclobutene for Multilayer Applications," *Proceedings of the ACS Division of Polymeric Materials: Science and Engineering*, 59, 190, 1988; P. H. Townsend et al., "The Processing and Properties of Multilayer Interconnection Structures Using Thermoset Films Derived From Bisbenzocyclobutene," *Proceedings of the Materials Research Society*, p. 47, 1989; J. Reche et al., "High Density Multichip Module Fabrication," *The International Journal for Hybrid Microelectronics*, Vol. 13, No. 4, 1990. Additional information on preparing multichip modules may be found in "Benzocyclobutene Processing Guide For Multilayer Interconnect Fabrication (Multichip Modules)," The Dow Chemical Company, Midland, Mich., 1991.

After being developed and spun dry, or post-baked, the remaining resin may be cured under a nitrogen atmosphere, using one of the following schedules:

For a soft cured film on which additional metal or polymer layers will be formed, one may heat at 210° C. for 40 minutes.

For a hard or finally cured film, one may heat according to the following schedule:
50° C. for 5 minutes
ramp from 50° C. to 100° C. over 15 minutes
100° C. for 15 minutes
ramp from 100° C. to 150° C. over 15 minutes
150° C. for 60 minutes
ramp from 150° C. to 250° C. over 60 minutes
250° C. for 1 minute
20° C. continuously.

The preferred 10 micron thick film may be fully cured at 250° C. for 60 minutes.

One may also cure the resin film in an infrared belt furnace. A suitable furnace and procedure are disclosed in P. E. Garrou et al., Rapid Thermal Cure of BCB Dielectrics, *Proceedings ECTC*, San Diego, May 1992, pp. 770–776. A Radiant Technology Corporation Model No. LA-306 infrared belt oven may be used with a nitrogen atmosphere. A soft cure may be obtained with a 1.5 minute residence at 260° C. A hard cure may be obtained with a 30 second residence at 280° C.

After curing the individual layers of DVS bis BCB resin formulation, one may remove any scum remaining in the interconnect vias by exposing the coated substrate to an $O_2/CF_4$ (90/10) plasma at 300 watts, 200 mTorr for 30 seconds. The need for this may vary depending on the size and shape of the vias and the amount of scum remaining.

For making a patterned cured resin film the following is recommended. The exemplified DVS bis BCB monomer is B-staged at a 25 weight percent solid in mesitylene for 46 hours at 165° C. and for sufficient time at 145° C. to obtain a viscosity of 4.4 cp at 145° C. (or 35 cSt at 25° C.) which should be equivalent to an Mw of 140,000 plus or minus 10,000. The DVS bis BCB resin is concentrated by vacuum stripping to 52 weight percent solids (viscosity 4,000 cp at 25° C.). The DVS bis BCB resin is formulated by adding 2 weight percent BAC-M, 0.75 weight percent 3,3'-diazidophenyl sulfone and 0.75 weight percent AgeRite MA antioxidant and diluting with mesitylene to a viscosity of 1100±50 cSt at 25° C.

This formulation may be spin-coated onto $SiO_2$, an underlying partially thermally cured DVS bis BCB resin formulation or copper on a substrate to form a 10 micron thick, patterned, cured, final film. Spin-coat at 68° F. to 70° F. and 45 to 55 percent relative humidity. Spread for 10 seconds at 500 rpm and spin for 30 seconds at 2800 rpm. Rinse the backside with xylene to prevent formation of cotton candy adhering to the edges of the substrate during spinning.

Prebake at 75° C. for 20 minutes. Photo expose through a mask with a super high pressure mercury arc, I-line (365 nm) at a dose of 300 to 600 mJ/cm². Form a puddle of Stoddard's solvent at 68° F. for 2 minutes and then rinse for 20 seconds while spinning at 500 rpm.

Remove residual developing solvent by post-baking at 100° C. for 1 minute and then cure. Soft cure at 210° C. for 40 minutes in $N_2$ if you want to add additional layers. Hard cure at 250° C. for 60 minutes in $N_2$ for a final cure. Descum any vias which need it by exposing the coated substrate to an $O_2/CF_4$ (90/10) plasma at 300 watts, 200 mTorr for 30 seconds.

This should yield a 10 micron thick patterned film.

One property that makes polymeric insulators useful in multichip module fabrication is their ability to planarize topographical features. The definition obtainable in photoresists is limited by the wavelength of the photon source employed and thus thickness variations can be detrimental to the quality of the module produced. For this reason it is important to have good planarization.

Illustrative Embodiments

The following examples are given to illustrate the invention and should not be interpreted as limiting it in any way. Unless stated otherwise, all parts and percentages are given by weight. All weight percents stated are relative to the weight of the resin present in the system, excluding the solvent and other additives unless otherwise noted. In examples where a resin is partially polymerized in a solvent, the percent resin solids are based on the weight of resin divided by the weight of resin plus solvent, multiplied by one hundred to obtain percent.

Unless otherwise noted, molecular weights given are apparent molecular weights obtained by size exclusion chromatography using linear polystyrenes as standards. The molecular weights are apparent because the DVS bis BCB resin is not linear and may have different response sensitivities to the detection means.

Procedure A:

Preparation of a Bisbenzocyclobutene Monomer represented by the formula:

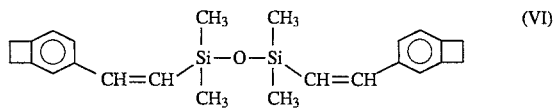
(VI)

The following reagents are used:

| | |
|---|---|
| 726 g | 3-bromobenzocyclobutene (3.97 mol) |
| 369 g | 1,3-divinyl-1.1,3,3-tetramethyl-disiloxane, (1.98 mol) |
| 1134 g | potassium acetate (11.56 mol) |
| 0.90 g | palladium acetate |
| 4.88 g | tri-(o-tolyl)phosphine |
| 1090 mL | N,N-dimethylformamide |
| 545 mL | deionized water |

Water is charged to the reactor and stirred. Potassium acetate is charged to the reactor and stirred until dissolved. N,N-dimethylformamide is charged to the reactor, followed by 3-bromobenzocyclobutene, 1,3-divinyl-1,1,3,3-tetramethyldisiloxane, palladium acetate and tri-(o-tolyl)phosphine. The resulting mixture is purged with a stream of nitrogen for 30 minutes. The reaction mixture is heated to 93° C. for 25 hours, at which time gas chromatographic analysis indicates that the reaction is complete.

The contents of the reactor are cooled to 60° C. and stirring is stopped. The reaction mixture is diluted with 1000 mL of deionized water. After phase separation has occurred, the water layer is removed and discarded.

The organic layer is diluted with 750 mL of Isopar® G hydrocarbon solvent. The organic phase is washed with 2500-mL portions of deionized water until the aqueous wash is neutral.

The organic phase is stirred during the addition of 2.9 g (0.032 mol) of tert-butyl hydroperoxide. The mixture is stirred at 60° C. for about 4 hours and then cooled to room temperature. A filter is prepared by packing a column of suitable size with 400 g of silica gel and 90 g of magnesium sulfate, on top of a 5 micron filter. The organic solution is passed through the column and the column is washed with 500 mL of Isopar® G hydrocarbon solvent.

The crude product is purified using a short-path distillation apparatus. Two passes are performed. In the first pass, crude product is degassed and Isopar® G hydrocarbon solvent and other volatiles are removed overhead at 110° C. to 130° C. and 4 to 25 mm Hg. In the second pass, at a temperature of 160° C. and a pressure of 0.001 mm Hg the DVS bis BCB monomer is removed overhead as the purified product leaving a tar fraction as a bottom stream.

Inorganic impurity content at various points of the purification procedure are:

TABLE 1

| Inorganic Specie | Crude ppm | Filtered ppm | Distilled ppm |
| --- | --- | --- | --- |
| Br | 159 | 10 | 1.9 |
| Cl | 3 | 7 | 3.3 |
| P | 600 | 100 | <0.3 |
| K |  | <0.3 | <0.3 |
| Na |  | <0.2 | <0.2 |

The distilled product may be sufficiently pure for use in electronic applications without further treatment.

EXAMPLE 1

Preparation of Photosensitive, Patterned Thin Films from
2,6-Bis(4-Azidobenzylidene)-4-Methylcyclohexanone and Oligomeric Divinyltetramethyldisiloxane Bisbenzocyclobutane A sufficient quantity of a 2,6-bis(4-azidobenzylidene)-4-methylcyclohexanone (BAC-M) (347.3 mg, 0.938 mmol) is added to a darkened vial containing oligomeric divinyltetramethyldisiloxane bisbenzocyclobutane (DVS bis BCB) (20.0636 g, 55 percent solids in mesitylene, 11.035 g polymer, Mw=31000, Mn=1300) to form a 3 percent solution of BAC-M. The vial is wrapped in aluminum foil and heated to 60° C. for 45 minutes to dissolve the BAC-M. The DVS bis BCB/BAC-M mixture is transferred to an Eberbach mixer and shaken for 40 minutes.

The DVS bis BCB/BAC-M solution is transferred to a class 1000 cleanroom for deposition on bare silicon wafers or substrates. Prior to deposition, the wafers are cleaned using a xylene stream applied to the wafer during a spin cycle. A stream of adhesion promoter, a 0.5 percent solution of triethoxyvinylsilylbenzocyclo-butane (TES-BCB), 3-aminopropyltriethoxysilane (3-APS), 3-methacryloxypropyl trimethoxysilane (MOPS), or triethoxyvinylsilane (TEVS), in water, is applied to the wafer for 2 seconds during a subsequent spin cycle using a syringe connected to a 0.2 µm filter, after which the wafer is spun dry.

Applying the DVS bis BCB/BAC-M solution to the substrate begins by pouring it onto the center of the stationary silicon substrate, which is then followed by a spin-coating step. The spin-coating procedure employed for the DVS bis BCB/BAC-M solution, using a Solitec Model 5100 spin-coater, involved two steps and produced a 5 µm coating after thermal cure. The first step is a spread cycle during which the substrate or wafer is spun at 500 rpm for 3 seconds to completely cover it with resin. The second step involved accelerating the substrate to 5000 rpm and holding it at that speed for 30 seconds.

The film close to the edge of the wafer, often called the edge bead, comprises concentric polymer rings that are somewhat thicker than the remainder of the film. The edge bead is removed using a xylene stream during a spin cycle. Edge bead removal increases the film thickness uniformity and makes manipulating the substrate easier.

Residual solvent not removed during the spin-coating process is removed using a softbake cycle in an oven containing a nitrogen atmosphere at 80° C. for 0.5 hours. After cooling to ambient temperature, the substrate is exposed for 5 minutes using a USHIO 250 watt medium-pressure mercury-xenon lamp contained within a Canon PLA501FA mask aligner through a patterned chrome-on-glass plated mask in the contact printing mode. The contact printing mode as used herein refers to direct contact between the mask and the film. This mode generally produces the highest resolution.

Solvent development, which is the dissolution and removal of film areas not exposed to photons, is effected by swirling the substrate while it is immersed in Stoddard solvent for 1 minute. Development produces the negative image in the film of the pattern contained on the mask which includes 10×10 µm vias.

The substrate is thermally cured under a nitrogen atmosphere using the following cure cycle.

50° C. to 100° C. over 5 minutes
100° C. for 15 minutes
100° C. to 150° C. over 15 minutes
150° C. for 15 minutes
150° C. to 250° C. over 1 hour
250° C. for 1 hour
250° C. to 100° C. over 2 hours The step height of the film as measured by profilometry, using a Tencor Instruments Alpha-Step 200 computerized surface profiler, is 2.48 µm, which is 48 percent of the control film thickness. The stylus mass used is 5 mg, the scan length 400 µm, and the scan rate is 5 µm/second.

EXAMPLE 2

Effect of Exposure Dose on Residual Film Thickness

A 3 percent solution of BAC-M in DVS bis BCB resin, prepared according to the procedure described in Example 1, is coated on a series of bare silicon wafers using the procedure described in Example 1. The substrates are exposed to the photon source of Example 1 for 1, 2, 3, 5, 10, and 15 minutes. The photon-exposed coated wafers are solvent developed using two immersion cycles of 30 seconds in Stoddard solvent. After a hard cure using the procedure described in Example 1, the film thickness is measured by stylus profilometry. Table 2 shows the effect of exposure dose on residual film thickness.

TABLE 2

Effect of Exposure Dose on Residual Film Thickness

| Exposure Time (Minutes) | Exposure dose (mJ/cm$^2$) | % Residual Film Thickness |
|---|---|---|
| 1 | 232.8 | 29.8 |
| 2 | 465.6 | 33.3 |
| 3 | 698.4 | 35.6 |
| 5 | 931.2 | 47.8 |
| 10 | 1164.0 | 46.5 |
| 15 | 3492 | 52.5 |

This data indicates that film thickness is influenced by exposure dose. Exposure time is a function of the photon source and preferably is minimized to increase throughput. The minimum exposure time is that necessary for the photons to penetrate the film sufficiently to cure the bottom layer of the film in contact with the substrate. Crosslinking at this interface prevents delamination of the polymer from the substrate.

EXAMPLE 3

Effect of Development Solvent Contact Time on Residual Film Thickness

A 3 percent solution of BAC-M in DVS bis BCB resin, prepared according to the procedure described in Example 1, is coated on a series of bare silicon wafers using the procedure described in Example 1. The films are exposed to the photon source for 15 minutes to ensure completion of the photochemical reaction. The wafers are quartered and one section is not developed thus serving as a control for the initial film thickness. The wafers are immersed in Stoddard solvent for different time periods. The films are dried under a nitrogen stream after development and thermally hard cured using the procedure described in Example 1. The film thickness of each sample, as measured by stylus profilometry, is shown in Table 3.

TABLE 3

Film Thickness as a Function of Development Time

| Development time(s) | Film Thickness (μm) | % Residual |
|---|---|---|
| 0 | 5.16 | 100 |
| 10 | 3.345 | 64.8 |
| 20 | 2.925 | 56.7 |
| 30 | 2.895 | 56.0 |
| 45 | 2.875 | 55.6 |
| 60 | 2.630 | 50.9 |
| 90 | 2.84 | 54.6 |
| 120 | 2.63 | 50.6 |
| 180 | 2.66 | 51.2 |

Table 3 shows that the majority of film thickness losses occur in the first 20 seconds of solvent development. This characteristic allowed for a wide range of development times with little effect on the film thickness.

EXAMPLE 4

Effect of Photosensitive Agent Concentration on Residual Film Thickness

One, two, three, and four percent solutions of BAC-M in DVS bis BCB-resin are coated on a series of bare silicon wafers using the procedure described in Example 1. The films are solvent developed for 1 minute in Stoddard solvent followed by hard curing. The film thicknesses differ as shown in Table 4.

TABLE 4

Variation in Film Thickness with % BAC-M

| % BAC-M | Film Thickness (μm) |
|---|---|
| 1 | 0 |
| 2 | 1.572 |
| 3 | 2.035 |
| 4 | 2.948 |

The data shows that film thickness can be increased by increasing the percent BAC-M.

EXAMPLE 5

Effect of Cosolvent on Normalized film Thickness

BAC-M (315.4 mg, 0.852 mmol, 5.4 percent) is added to a darkened vial containing oligomeric DVS bis BCB-(9.9974 g, 55 percent solids in mesitylene, 5.498 g polymer, Mw=27100, Mn=1300) in a darkened laboratory. A 0.5353 g portion of 2-methoxyethanol is added to dilute the polymer to 52.2 percent solids based on the sum of the weights of polymer and solvents. After shaking on an Eberbach mixer for five minutes at a high setting, the solution is heated at 60° C. for 0.5 hours. The sample is shaken on the high setting for 0.5 hours as it is cooled to ambient temperature. The agitation and heating cycles are repeated followed by a 5 hour shake at a low setting, after which the BAC-M is fully solubilized.

Additional solutions are prepared at 6.3 percent BAC-M (370.4 mg), and 7.3 percent BAC-M (435.4 mg) using 0.5247 and 0.5314 g of 2-methoxyethanol, respectively. The 6.3 percent sample is almost completely soluble and the 7.3 percent sample even less soluble. Additional methoxyethanol, 0.2858 g and 0.5010 g, is added to the 6.3 percent and 7.3 percent BAC-M samples, respectively. After shaking on an Eberbach mixer for 5 minutes on the high setting, the solutions are heated at 60° C. for 0.5 hours. The samples are shaken for 0.5 hours on a high setting as they are cooled to ambient temperature. This procedure completely solubilizes the 6.3 percent sample, but not the 7.3 percent sample.

Film preparation is performed as described in Example 1, except that solvent development is performed by spraying the wafer with solvent thereby forming a puddle of solvent on the wafer. The wafer is stationary for 5 seconds followed by the spread and spin cycles of Example 1. The samples are thermally hard cured using the procedure described in Example 1. The film thickness of each sample, as measured by stylus profilometry, is shown in Table 5.

TABLE 5

Normalized Film Thickness as a Function of % BAC-M

| % BAC-M | Normalized Film Thickness |
|---|---|
| 1 | 7.3 |
| 2 | 27.3 |
| 3 | 37.1 |
| 4 | 50.2 |
| 5 | 64.4 |
| 6 | 64.1 |
| 7 | 70.8 |

This data shows that the normalized (compared to a control for each percent BAC-M solution) film thickness increased significantly when increased in the percent BAC-M. Using 2-methoxyethanol permits BAC-M dissolution at 5 and 6 weight percent in a mesitylene solution containing polymer at 55 percent solids. Such levels are not reproducibly attainable using mesitylene alone.

EXAMPLE 6

Effect of Resin Molecular Weight on Film Retention

A 27,100 weight-average molecular weight DVS bis BCB resin is subjected to the same film preparation, exposure, solvent development, and analysis as described in Example 1. The thermal cure cycle is as follows.

50° C. for 0.5 hour

50° C. to 250° C. over 1 hour

250° C. for 1 hour

250° C. to 100° C. over 2 hours

The residual film thickness of this system is 36.3 percent of the control film thickness.

A 44,000 Mw DVS bis BCB resin (Mn=1360) is prepared by increasing the extent of conversion by B-staging for a longer time period. It is diluted to 55 percent solids to allow a valid film retention comparison to the previously described film system comprising a 27,100 molecular weight polymer. This is done by diluting with mesitylene and shaking for 1 hour using an Eberbach mixer on the high setting prior to adding the 3 percent BAC-M. The light sensitive formulation is prepared by the procedure described in Example 1. The residual film thickness of this system is 48.3 percent of the control film thickness.

A 73,000 Mw DVS bis BCB resin (Mn=1400) is prepared by further increasing the extent of conversion by B-staging. This material surpasses its gel point. The gels are removed by filtration. It is diluted to 55 percent solids with mesitylene and shaken for 1 hour using an Eberbach mixer on the high setting prior to adding the 3 percent BAC-M photosensitive agent. The 3 percent BAC-M is added under amber filtered yellow lights to prevent premature photo-curing of the mixture. After dissolving the BAC-M, the mixture is taken to a class 1000 clean room having filtered amber lights and is subjected to the same coating, softbake, exposure, solvent development, and hard cure as the two previous examples. Surface profilometry indicated the resultant film retained 58.2 percent of the initial film thickness.

These three examples demonstrate that film retention is increased by increasing the cyclobutarene resin molecular weight.

EXAMPLE 7

Effect of Varying the Oligomer Percent Solids Content

The 73,000 molecular weight DVS bis BCB resin from Example 6 is used at 60 percent solids, in the following protocol. BAC-M (377.7 mg, 1.02 mmol, 3.0 weight percent) is added to a darkened vial containing oligomeric DVS bis BCB (20.0022 g, 60 percent solids in mesitylene, 12.0013 g polymer, Mn=1,400, Mw=73,000) in a darkened laboratory. The vial is wrapped in aluminum foil and heated for 45 minutes in an oven at 60° C. The sample is removed from the oven and shaken on an Eberbach mixer at a high setting for 20 minutes as it cooled to ambient temperature.

After treatment with spread and spin cycles and softbake conditions as described in Example 1, the wafer is exposed to the photon source described in Example 1 for 15 minutes through a mask. The wafer is quartered and one section not developed thereby serving as a reference for the initial film thickness. One section is immersion developed for 30 seconds in Stoddard solvent. All of the films are thermally hard cured as described in Example 6.

The film's masked areas that are solvent developed with Stoddard solvent are 8.4 μm thick as measured by stylus profilometry, which translates to a 27.9 percent film loss relative to the undeveloped portion which measures 11.55 μm. This film retention of 72.1 percent at 60 percent solids can be compared to the 58.2 percent film retention of the 55 percent solids 73,000 molecular weight system of Example 6.

This data indicates that higher polymer solids loadings in mesitylene produces thicker polymer coatings. At excessive solids loadings, fibers form which emanate over the edge of the wafer which can complicate processing.

The aspect ratio of this film system, as measured by electron microscopy, is approximately 0.5 for a 9.1 μm high line separated by 18.2 μm from its nearest neighboring feature.

EXAMPLE 8

Effect of the DVS bis BCB Molecular Weight Distribution on Film Retention

The oligomeric DVS bis BCB of Example 5 (40.0 g, 55 percent solids in mesitylene, 22.0 g polymer, Mn=1300, Mw=27100) is placed in an addition funnel positioned high enough above a blender of rapidly stirring isopropanol to prevent oligomer precipitation prior to transferring the oligomer mixture to the blender. The oligomer mixture is added dropwise to the blender being operated at a high shear rate over a 75 minute period. A white precipitate is formed which is removed from the blender using a spatula and filtered using a medium porosity fritted funnel and a water aspirator as a vacuum source. The precipitate is dried at 50° C. for 8.5 hours in a vacuum oven attached to a vacuum source of less than 30 inches of Hg. The resulting white amorphous glassy material is pulverized using a mortar and pestle thus producing 20.1 g (91.4 percent recovery) of a nontacky white powder. Size exclusion chromatography indicated that the molecular weight distribution (Mn=1,700, Mw=31,000) is changed such that the monomer content is reduced from 12.9 percent to 7.4 percent and the dimer content reduced from 10.7 percent to 9.7 percent. Film retention in this system is 42.7 percent following photon exposure and solvent development procedures described in Example 1. This is in comparison to the film retention of 36.3 percent for the polymer system of Example 6 wherein there is no change of the molecular weight distribution.

EXAMPLE 9

Comparison of Spray and Immersion Development

A series of DVS bis BCB oligomeric solutions containing 1–4 percent BAC-M are prepared as described in Example 4. One group is spray-developed while the second is immersion-developed. The results shown in Table 6 indicate that the two procedures produce similar film thicknesses.

Spray-development is effected by spraying a stream of Stoddard solvent onto the center of the wafer during spin and spread cycles of 33 seconds followed by a spin cycle to dry the wafers.

Immersion-development is effected by swirling the wafers in Stoddard solvent for 60 seconds as described in Example 1 followed by drying the wafers under a nitrogen stream.

TABLE 6

Film Thickness as a Function of Development Method

| % BAC-M | Thickness ($\mu m$) Spray | Thickness ($\mu m$) Immersion |
| --- | --- | --- |
| 1 | 0 | 0 |
| 2 | 1.69 | 1.57 |
| 3 | 2.16 | 2.04 |
| 4 | 2.95 | 2.66 |

EXAMPLE 10

Effect of Varying the Developing Solution

A 3.0 percent solution of BAC-M (426.3 mg) in oligomeric DVS bis BCB (24.9700 g, 55 percent solids in mesitylene, 13.7335 g polymer) is prepared by the procedure described in Example 5. Films are prepared from this solution according to the procedure described in Example 1 with the exception that the adhesion promoter in this system is triethoxyvinyl silane in acetic acid which is prepared as a 0.5 percent solution in deionized water. This solution is aged for a minimum of 15 minutes prior to use and can be used for a maximum of 8 hours after preparation. After a thermal cure according to the procedure of Example 6, the film thickness is measured by stylus profilometry relative to a control wafer for each of the developing solutions. The results are shown in Table 7.

TABLE 7

Film Thickness as a Function of Developing Solution

| Developer | Thickness ($\mu m$) | % Retention |
| --- | --- | --- |
| Stoddard solvent | 1.76 | 33.1 |
| Mesitylene | 1.92 | 35.6 |
| Xylene | 1.68 | 31.2 |

This data indicates that a variety of materials can be used for solvent development of these films. Optimization of the developing solution is possible by adding nonsolvents such as methanol or isopropanol as a means of slowing the film removal rate, thereby retaining a greater percentage of the initial film thickness.

EXAMPLE 11

Preparation of Photosensitive, Patterned Thin Films From 2,6-Bis(4-Azidobenzylidene)-4-Methylcyclohexanone and Oligomeric 3,3'-(Ethenyl)Bis-bicyclo(4.2.0)Octa-1,3,5-Triene A 60 percent solids solution of oligomerized 3,3'-(ethenyl)bis-bicyclo(4.2.0)octa-1,3,5-triene (9.9722 g total, 5.9833 g polymer, Mn=600, Mw=2000) in xylene is combined with 420 mg of 2,6-bis(4-azidobenzylidene)-4-methylcyclohexanone (BAC-M) under amber lights. The solution is shaken for 20 minutes on an Eberbach mixer set on its highest speed. The solution is then heated to 60° C. and held at that temperature for 30 minutes thereby producing a homogeneous solution. After cooling to ambient temperature over 30 minutes, additional BAC-M (608.7 mg total, 9.2 percent) is added to the solution which is then heated for an additional 30 minutes at 60° C. The resulting solution, containing some insoluble material, is coated onto substrates using the procedure described in Example 1. The film coated substrates are heated in a nitrogen atmosphere to 120° C. and maintained at that temperature for 30 minutes. After a 5 minute cool down period they are immersion-developed for 1 minute in mesitylene. The resulting film-coated substrates are cured using the thermal cure cycle described in Example 6. Profilometry results indicate that the developed films have step heights of 4.148 $\mu m$ while the photon-exposed, undeveloped control films have a thickness of 4,147 $\mu m$.

EXAMPLE 12

Preparation of Photosensitive, patterned Thin Films From 2,6-Bis(4-Azidobenzylidene)-4-Methylcyclohexanone and an Equimolar Mixture of Oligomeric 3,3'-(Ethenyl)Bis-Bicyclo(4.2.0)Octa-1,3,5-Triene and Divinyltetramethyldisiloxane Bisbenzocyclobutane A 55 percent solids solution of oligomerized 3,3'-(ethenyl)bis-bicyclo(4.2.0)octa-1,3,5-triene/divinyltetramethyldisiloxane bisbenzocyclobutane copolymer (EL-BCB/DVS bis BCB) (9.1922 g total, 5.0557 g polymer) in xylene is combined with 402.5 mg of 2,6-bis(4-azidobenzylidene)-4-methylcyclohexanone (BAC-M) under amber lights. The solution is shaken for 20 minutes on an Eberbach mixer set on its highest speed. The solution is then heated to 60° C. and held at that temperature for 30 minutes thereby producing a homogeneous solution. After cooling to ambient temperature over 30 minutes, additional BAC-M (515.8 mg total, 113.3 mg BAC-M, 9.3 percent) is added to the solution which is then heated for an additional 30 minutes at 60° C. The resulting solution, containing some insoluble material, is coated onto substrates using the procedure described in Example 1. The film coated substrates are heated in a nitrogen atmosphere to 120° C. and maintained at that temperature for 30 minutes. After a 5 minute cool down period, they are immersion-developed for 1 minute in Stoddard solution. The resulting film coated substrates are cured using the hard cure cycle described in Example 6. Profilometry results indicate that the developed films have step heights of 4.135 $\mu m$ while the photon-exposed, undeveloped control films have a thickness of 5,492 $\mu m$.

EXAMPLE 13

Preparation of Photosensitive, Patterned Thin Films from 2,6-Bis(4-Azidobenzylidene)-4-Methylcyclohexanone, Oligomeric Divinyltetramethyldisiloxane Bisbenzocyclobutane and Polymerized 1,2-Dihydro-2,2,4-Trimethylquinoline Under amber filtered lights BAC-M (174.4 mg, 0.47 mmol, 3.0 weight percent) is added to an amber vial containing a 1 percent solution of polymerized 1,2-dihydro-2,2,4-trimethylquinoline (PDTQ) in oligomeric DVS bis BCB (10.2128 g, 55 percent solution in mesitylene, 5.5614 g polymer, 55.6 mg PDTQ). The mixture is dissolved and processed by the procedure described in Example 10. Stoddard solvent is used as the immersion developer for 1 minute.

A second mixture is prepared using an antioxidant comprising PDTQ modified by aromatization or hydrogenation (PDTQ-M). BAC-M (159.9 mg, 0.43 mmol, 3.1 weight percent) is added to an amber vial containing a 1 percent solution of PDTQ-M in oligomeric DVS bis BCB (9.2418 g, 55 percent solution in mesitylene, 5.0327 g polymer, 50.3 mg PDTQ-M). The mixture is processed according to the procedure described for PDTQ. The profilometry results for these films are shown in Table 8.

TABLE 8

| | Antioxidant Effect on % Film Retention | | |
|---|---|---|---|
| Antioxidant | Film Thickness (μm) | Control Film Thickness (μm) | % Retention |
| PDTQ | 1.414 | 4.886 | 28.9 |
| PDTQ-M | 1.639 | 5.612 | 29.2 |

This data suggests that antioxidants do not drastically affect the film retention of photodefinable mixtures.

EXAMPLE 14

Effect of Photosensitizer 3,3'-Carbonyl Bis(7-Diethylaminocoumarin)

Meta-azidophenyl sulfone (0.4331 g, 300.30 g/mol, 1.44 mmol, 3.0 weight percent) and 3,3'-carbonyl bis(7-diethylaminocoumarin) (0.0730 g, 460.53, 0.16 mmol) are added under amber filtered lights to an amber vial containing a solution of oligomeric DVS bis BCB (25.3257 g, 55 percent solids in mesitylene, 13.9291 g polymer). The vial is capped and heated in a water bath at 60° C. for 1 hour. The bisazide is not completely soluble at this point. The mixture is heated at 60° C. for an additional ½ hour. The sample is shaken for 1 hour using an Eberbach shaker on a high setting resulting in a homogeneous solution.

A 4 inch silicon wafer is spin-coated with the solution at a spin speed of 5,000 rpm for 30 seconds. The wafer is softbaked at 80° C. for ½ hour under nitrogen. Prior to exposure, the wafer is cooled to room temperature. It is exposed to 350 to 450 nm UV light for 15 seconds using a 1,000 watt high pressure mercury-xenon arc lamp, and then immersion-developed for 2 minutes using Stoddard solvent. The wafer is then thermally cured ($T_{max}=250°$ C.). After solvent development and cure, profilometry results indicate a film thickness of 4.1 microns.

A UV-Vis spectrum of a DVS bis BCB solution from 300 nm to 500 nm at a scan rate of 60 nm per minute is very similar to that obtained for a DVS bis BCB/bisazide mixture, thus indicating that this bisazide absorbed in the same region as the DVS bis BCB, which is at lower wavelength than desired.

The significance of these results is that the bisazide (meta-azidophenyl sulfone)/DVS bis BCB mixture without photosensitizer is not curable by exposure to 350 to 450 nm UV light, however, when 0.5 percent of photosensitizer is added the sensitivity of the mixture increases significantly.

Very similar results are obtained when the 3,3'-carbonyl bis(7-diethylaminocoumarin) photosensitizer is replaced with 3,3'-carbonyl bis(7-dimethoxycoumarin).

EXAMPLE 15

Effect of Precipitating Oligomeric DVS Bis BCB in Refluxing alcoholic solvents

Oligomeric DVS bis BCB (40.5 g, 60 percent solids in mesitylene, 24.3 g polymer, Mw=44000, Mn=1360) is placed in a pressure-equalizing addition funnel connected to a Claisen adapter which is inserted into a 3-necked 1000 mL resin kettle containing 700 mL of isopropanol. The resin kettle is equipped with an immersion well to control the solution temperature and a reflux condenser, equipped with a nitrogen outlet, which is connected to the portion of the claisen adapter not directly above the stirring solution. The resin kettle is purged with nitrogen for 15 minutes prior to heating and continuously purged at a slow rate thereafter. The isopropanol is brought to reflux prior to the addition process. The oligomer is added dropwise over a period of 113 minutes to the solution which is stirred at 300 rpm using a mechanical stirrer equipped with polytetrafluoroethylene-coated blades at both the bottom and top of the isopropanol solution. After addition is completed, the mixture is stirred for an additional 15 minutes prior to removing the stirring and heating sources. After sitting for 16 hours overnight, the apparatus is disassembled and the mixture filtered. The solids are washed with three 50-mL portions of isopropanol and removed using a spatula. The resin is pulverized using a mortar and pestle to increase the surface area of the solid to facilitate drying. The resin is dried in a vacuum oven at 50° C. for 2 hours and then at 90° C. for 18 hours to remove any residual isopropanol and consolidate the resin. The resin collapses indicating that the polymer's glass transition temperature is 90° C. or below. The high molecular weight material recovered weighed 16.4 g (67.5 percent).

The soluble components of this separation are concentrated using a rotary evaporator giving 8.1 g of viscous resin for later characterization by size exclusion chromatography. The overall material balance is 16.4+8.1 g=24.5 g (101 percent) indicating that very little isopropanol is left in the low molecular weight component.

The resulting change in the molecular weight distribution is from Mn=1300, Mw=40000 to Mn=4100, Mw=57000. The polymer is redissolved in mesitylene at 55 percent solids after heating at 60° C. for 1 hour. A 3 weight percent BAC-M formulation is prepared and films produced therefrom by spin coating at 5000 rpm. After immersion-development for 1 minute in Stoddard solvent and cure, the film thickness of the patterned film is 7.2 μm (66 percent film retention) with a control film thickness of 10.9 μm compared to the 5 μm coating produced from 55 percent solutions of the unaltered material.

Using polymer precipitated in isopropanol results in a nearly complete removal of the monomeric and dimeric components of the resin. However, the film loss of approximately 33 percent described above indicated that higher oligomeric materials are responsible for some loss. Therefore, in an effort to remove a greater quantity of the higher molecular weight oligomers, high boiling alcohols are used producing the data in Table 9.

TABLE 9

Polymer Precipitation Results: Characterization of Precipitated B-staged DVS-BCB

| Alcohol | b.p. °C. | Dielectric Constant | Mn | Mw | Monomer (%) | Dimer (%) | % Recovery |
|---|---|---|---|---|---|---|---|
| NONE | | | 1300 | 38500 | 12.2 | 10.6 | NA |
| Isopropyl | 82.3 | 18.3 | 4100 | 57000 | 1.3 | 2.2 | 67.5 |
| t-butyl | 83 | 10.9 | 5700 | 74000 | 1.2 | 1.7 | 51.8 |
| 2-butyl | 99–100 | 15.8 | 5300 | 73000 | 1.2 | 1.8 | 58.4 |
| 1-pentyl | 136–138 | 13.9 | 6100 | 72000 | 1.5 | 1.6 | 47.7 |
| 2-pentyl | 119–120 | 14.2 | 6600 | 71000 | 1.1 | 1.4 | 51.0 |
| 3-methyl 1-butyl | 130 | 14.7 | 5900 | 87000 | 1.2 | 1.6 | 53.9 |
| 3-methyl 2-butyl | 112 | | 7100 | 83000 | 1.0 | 1.4 | 50.4 |
| 2-methyl 2-butyl | 102 | 5.82 | 8100 | 99000 | 1.2 | 1.4 | 41.1 |
| 2-methyl 1-butyl | 130 | | 6400 | 67000 | 1.0 | 1.5 | 53.1 |

The most preferred alcohol for precipitating the higher molecular weight oligomeric components of DVS bis BCB is t-amyl alcohol (2-methyl 2-butyl), which removes a portion of the DVS bis BCB trimer.

Removing the low molecular weight components results in both greater film retention and greater film thickness at the same solids concentration.

EXAMPLE 16

Effect of Solvent Precipitated DVS bis BCB Resin Molecular Weight on Percent Film Retention A 57,000 weight average molecular weight DVS bis BCB resin is prepared by the same preparation method as described in Example 15 using isopropyl alcohol as the extraction solvent and is subjected to the same film preparation, solvent development, and analysis as described in Example 1. 2-Methoxyethyl ether is used as a development solvent for a development time of 90 seconds and the wafers are given an exposure dose of 1,000 mJ/cm$^2$ at the 365 nm wavelength. The films are spun at a spin speed of 5,000 rpm after a 10 second spread cycle at 500 rpm. The thermal cure cycle is as follows:

50° C. for 5 minutes

50° C. to 100° C. over 5 minutes

100° C. for 15 minutes

100° C. to 150° C. over 15 minutes

150° C. for 15 minutes

150° C. to 250° C. over 60 minutes

250° C. for 60 minutes

250° C. to 100° C. over 120 minutes

The residual film thickness of this system is 58.8 percent of the control film thickness after development and 60.8 percent after cure.

In an effort to maximize the film retention after development and cure, other high molecular weight resins that are prepared as described in Example 15 using various alcohols for precipitation. The resins are evaluated producing the data in Table 10.

TABLE 10

Percent Film Retention of Precipitated B-staged DVS-BCB Resins

| Precipitating Alcohol | Mw | Mn | Film Thickness After Development (μm) (% Retention) | Film Thickness After Cure (μm) (% Retention) |
|---|---|---|---|---|
| isopropyl | 57,000 | 4,100 | 2.62 (58.8) | 2.72 (60.9) |
| 2-methyl,1-butanol | 67,000 | 6,400 | 3.89 (72.3) | 3.97 (73.8) |
| 2-pentanol | 71,000 | 6,600 | 4.34 (75.5) | 4.42 (77.0) |
| 1-pentanol | 72,000 | 6,100 | 4.32 (78.0) | 4.41 (79.7) |
| 2-butanol | 73,000 | 5,300 | 3.14 (61.8) | 3.33 (65.6) |
| 3-methyl,2-butanol | 83,000 | 7,100 | 4.57 (79.1) | 4.65 (80.5) |
| 3-methyl,1-butanol | 87,000 | 5,900 | 4.00 (71.6) | 4.14 (74.2) |
| t-amyl | 99,000 | 8,100 | 5.51 (86.6) | 5.57 (87.5) |
| t-amyl | 128,000 | 4,900 | 5.63 (87.4) | 5.76 (89.4) |

The most preferred resin for obtaining films with good film retention after development and cure is the resin precipitated in t-amyl alcohol (2-methyl, 2butyl alcohol) which has a film retention of 86.6 percent after development and 87.5 percent after cure.

The higher the weight average and number average molecular weight of the DVS bis BCB resin the greater the film retention after development and cure.

EXAMPLE 17

Effect of Film Thickness on Film Retention

Oligomeric DVS bis BCB (567.6 g, 56 percent solids in mesitylene, 317.8 g solids) is poured into a pressure equalizing addition funnel. The addition funnel is connected to a 5 L resin kettle with a bottom drain. Tertiary-amyl alcohol (3.5 L, Aldrich, 99 percent) is added to the 5 L reaction flask. The reactor is purged with nitrogen slowly throughout the remainder of the procedure. The alcohol is heated to reflux (bp. 102° C.) and the polymer solution is added. After the addition is completed, the reactor cooled to 35° C. over a period of approximately 3 hours. The homogeneous polymer solution became cloudy at 71° C. A white high density fraction settled to the bottom of the reactor. Subsequently, the viscous white resin is decanted through the stopcock. After the decantation is completed, the material is dried inside a vacuum oven at 110° C. for 15 h producing 129.8 g (40.8 percent) of a white polymer.

The procedure is repeated nine additional times and the resultant polymer mixed together to give a masterbatch of material with the following molecular weight distribution: Mn 4800, Mw 95,000 and Mz 295,000.

A 3 percent BAC-M formulation is prepared as described in Example 1. Prior to polymer deposition, an adhesion promoter, 3-aminopropyltriethoxysilane (3-APS), is applied as a 0.5 percent aqueous solution (w/w) at 5000 rpm.

The resin is spin-coated on 100 mm silicon wafers using a spread cycle at 500 rpm for 10 seconds in which the polymer solution flowed out to cover the substrate followed by a final spin speed (variable see Table 11) which is maintained for 30 seconds. After exposure (1000 mJ/cm$^2$ at 365 nm wavelength), the films are developed using an appropriate solvent. The film thickness is measured after development and after the final cure for developed films. The control film thickness is measured after cure which is preceded by exposure.

TABLE 11

Film Thickness for 3 Weight Percent BAC-M/DVS-bis-BCB Solutions (10 second spread time)

| % Solids | RPM Spin Speed | Film Thickness (μm) Control | Film Thickness (μm) After Dev. | Film Thickness (μm) After Cure | Percent Retention |
|---|---|---|---|---|---|
| \multicolumn{6}{c}{Developed in Stoddard Solvent} ||||||
| 45 | 2000 | 9.253 | 9.685 | 8.319 | 89.9 |
|    | 3500 | 6.914 | 6.185 | 5.895 | 85.3 |
|    | 5000 | 5.718 | 5.420 | 4.940 | 86.4 |
| \multicolumn{6}{c}{Developed in Diglyme} ||||||
| 45 | 2000 | 9.285 | 8.085 | 8.110 | 87.3 |
|    | 3500 | 6.870 | 5.800 | 5.835 | 84.9 |
|    | 5000 | 5.700 | 4.870 | 4.895 | 85.9 |

EXAMPLE 18

Thicker Films by Multiple Coatings and Exposures Followed by one Solvent Development Step In an attempt to obtain thicker photopatterned polymer coatings, a multiple photopolymer coating and exposure process is developed.

1,006 grams of an oligomer of 1,2-dihydro-2,2,4-trimethylquinoline available as AgeRite MA is added to 199.358 grams of a 50 percent solids DVS bis BCB resin (molecular weight of Mn=4,500 g/mole; Mw=59,000 g/mole) solution in mesitylene and dissolved with heating at 60° C. in a water bath shaker for 1 hour. 3.085 g of BAC-M is added to the solution and dissolved with heating at 60° C. in a water bath shaker for 30 minutes. The solution is then filtered through a 0.5 micron filter.

A clean silicon wafer with patterned aluminum metal deposited on top of the thermal silicon oxide, is spin-coated with a 0.5 percent aqueous solution of 3-aminopropyltriethoxysilane adhesion promoter at a spin speed of 2,500 rpm for 30 seconds. The photodefinable solution is then spin-coated using a 10 second spread cycle of 500 rpm followed by a spin speed of 2,500 rpm for 30 seconds to yield a 8.0 micron thick film. The wafer is placed in a nitrogen purged oven at 80° C. for 30 minutes. After cooling to room temperature, the wafer is placed in an Oriel mask aligner and the aluminum pattern on the wafer is aligned to the photomask. The photodefinable DVS bis BCB film on the wafer is then given an exposure dose of 700 mJ/cm$^2$ of light measured at the 365 nm wavelength (broad band source 350 to 450 nm). A second photodefinable DVS bis BCB film is spin-coated on the first exposed film at a spin speed of 7,500 rpm to give a film coating thickness of 8.0 microns. The wafer is placed in a nitrogen purged oven at 80° C. for 30 minutes. After cooling to room temperature, the wafer is placed in an Oriel mask aligner and the aluminum pattern on the wafer is aligned to the photomask. The second photodefinable film is given an exposed dose of 700 mJ/cm$^2$ measured at the 365 nm wavelength (broad band source 350–450 nm). The wafer is then immersed in 2-methoxyethyl ether for 90 seconds and sprayed dry with a nitrogen stream. The wafer is placed in a nitrogen purged oven at 80° C. for 10 minutes to further dry. The total film thickness for the photodefinable DVS bis BCB is measured using a profilometer by dragging the profilometer stylus over a via hole patterned into the film. The film thickness after development is approximately 12.23 microns. The film is cured according to the following cure schedule:

50° C. for 5 minutes
50° C. to 100° C. over 5 minutes
100° C. for 15 minutes
100° C. to 150° C. over 15 minutes
150° C. for 15 minutes
150° C. to 250° C. over 60 minutes
250° C. for 60 minutes
250° C. to 100° C. over 120 minutes The cured polymer film is continuous and of high quality with a film thickness of 12.93 microns.

EXAMPLE 19

Thicker Films by Use of A DVS Bis BCB Formulation With a Mixture of Bisazides In an attempt to decrease the optical density and maintain high film retention after development and cure a DVS bis BCB formulation with a mixture of bisazides is used.

0.134 Grams of m-azidophenyl sulfone (m-sulfone) is added to 24.040 grams of a 55.6 percent solids DVS bis BCB resin (molecular weight of Mn=4,500 g/mole; Mw=59,000 g/mole) solution in mesitylene and dissolved with heating at 60° C. in a water bath shaker for 30 minutes. The solution is then placed in the sonicator for 30 minutes and then back into a water bath shaker at 60° C. for 30 minutes to help dissolve the m-azidophenyl sulfone. 0.269 Grams of BAC-M is added to the solution and dissolved with heating at 60° C. in a water bath shaker for 30 minutes. The solution is then placed in the sonicator for 20 minutes and filtered through a 5.0 micron filter into a clean amber bottle.

0.266 Grams of BAC-M is added to 23.767 grams of a 55.6 percent solids DVS bis BCB resin (molecular weight of Mn=4,500 g/mole; Mw=59,000 g/mole) solution in mesitylene and dissolved with heating at 60° C. in a water bath shaker for 30 minutes. The solution is then placed in the sonicator for 20 minutes. Both solutions are formulated at the same time.

250° C. for 60 minutes

250° C. to 100° C. over 120 minutes

The film thickness after cure is 9.450 microns as determined by a profilometer.

In an effort to maximize the film retention and film thickness after development and cure, other wafers are spin-coated with the 1 percent m-azidophenyl sulfone/2 percent BAC-M solution at various spin speeds. For comparative purposes, the solution with 2 percent BAC-M is also evaluated at the same spin coating conditions. The resins are evaluated for film thickness after each processing step as described above producing the data in Table 12.

TABLE 12

| | | Film Thickness and Percent Film Retention During Processing | | | | |
|---|---|---|---|---|---|---|
| Solution | Spin Speed | Pre Development Film Thickness | Post Development Film Thickness | Post Development % Film Retention | Post Cure Film Thickness | Post Cure % Film Retention |
| 2% BAC-M | 3000 | 10.60 | 8.430 | 79.53% | 8.720 | 82.26% |
| 2% BAC-M | 3000 | 10.52 | 8.430 | 80.13% | 8.625 | 81.99% |
| 2% BAC-M/ 1% m-SULFONE | 3000 | 10.83 | 9.220 | 85.13% | 9.450 | 87.26% |
| 2% BAC-M/ 1% m-SULFONE | 3000 | 10.84 | 9.325 | 86.02% | 9.525 | 87.87% |
| 2% BAC-M | 3250 | 10.15 | 8.255 | 81.33% | 8.400 | 82.76% |
| 2% BAC-M | 3250 | 10.19 | 7.855 | 77.09% | 8.140 | 79.88% |
| 2% BAC-M/ 1% m-SULFONE | 3250 | 10.33 | 8.655 | 83.79% | 8.910 | 86.25% |
| 2% BAC-M/ 1% m-SULFONE | 3250 | 10.40 | 8.840 | 85.00% | 8.965 | 86.20% |
| 2% BAC-M | 3500 | 9.760 | 7.745 | 79.35% | 7.935 | 81.30% |
| 2% BAC-M | 3500 | 9.760 | 7.630 | 78.18% | 7.960 | 81.56% |
| 2% BAC-M/ 1% m-SULFONE | 3500 | 9.995 | 8.440 | 84.44% | 8.695 | 86.99% |
| 2% BAC-M/ 1% m-SULFONE | 3500 | 9.985 | 8.335 | 83.48%% | 8.555 | 85.68% |

A clean silicon wafer is spin-coated with a 0.5 percent aqueous solution of 3-aminopropyltriethoxysilane adhesion promoter at a spin speed of 3,000 rpm of 30 seconds. The 1 percent m-azidophenyl sulfone/2 percent BAC-M solution is then spin-coated on the wafer using a 10 second spread cycle of 500 rpm followed by a spin speed of 3,000 rpm for 30 seconds to yield a 10.83 micron thick film. The wafer is placed in a nitrogen purged oven at 80° C. for 30 minutes. After cooling to room temperature, the wafer is placed in an Oriel mask aligner and the photodefinable DVS bis BCB film on the wafer is then given an exposure dose of 1,000 mJ/cm$^2$ of light, measured at the 365 nm wavelength, (broad band source 350 to 450 nm) through a quartz photomask. The film thickness is measured with a profilometer to be 10.83. The wafer is then immersed in 2-methoxyethyl ether for 90 seconds and sprayed dry with a nitrogen stream. The wafer is placed in a nitrogen purged oven at 80° C. for 10 minutes to further dry. After solvent development and drying, the film thickness is 9.22 microns as measured by a profilometer. The film is cured according to the following cure schedule:

50° C. for 5 minutes

50° C. to 100° C. over 5 minutes

100° C. for 15 minutes

100° C. to 150° C. over 15 minutes

150° C. for 15 minutes

150° C. to 250° C. over 60 minutes

The most preferred resin for obtaining films with good film retention after development and cure is the resin containing 1 percent m-azidophenyl sulfone and 2 percent BAC-M which has a film retention of 85.13 percent after development and 87.26 percent after cure for a starting film thickness of 10.83 microns.

EXAMPLE 20

Use of a Bisazide with Extended Conjugation 2,6-Bis[3-(4-azidophenyl)-2-propenylidene]- 4-methylcyclohexanone of the structure:

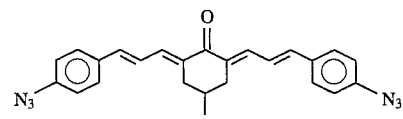

2,6-Bis[3-(4-azidophenyl)-2-propenylidene]-4-methylcyclohexanone (0.110 g, 2 weight percent based on polymer) is added to an ambered vial followed by N-methyl pyrrolidone (2.118 g). The vial is capped and shaken by hand in order to dissolve the material. DVS bis BCB (10.019 g, 54.5 percent solids, 5.461 g polymer, adjusted percent solids: 45.0, molecular weight: Mn=4500 g mol$^{-1}$, Mw=59,000 g mol$^{-1}$) is added and the mixture is heated at 60° C. for 18 minutes in a water bath shaker while rotating at 150 rpm. The solution is mixed vigorously be shaking by hand for 1 minute. After sonication to remove bubbles for 1 minute, a homogeneous solution is obtained. The material is permitted to cool to room temperature.

Inside the clean room, the material is spin-coated and processed using conditions similar to Example with the following modifications:

1. A spin speed of 3500 rpm is used.
2. The material is exposed for 1000 mJ/cm$^2$ (measured at 365 nm, 17.9 s) followed by development in Stoddard solvent (immersion, 3 minutes). The film is dried using a stream of nitrogen followed by heating on a hot plate at 80° C. for a few minutes to further dry the film.

Film thickness is determined after exposure and development or for the control substrate, after bake and exposure. The film thicknesses are also determined after the cure schedule used in Example 19.

| Film Thickness Results | |
| --- | --- |
| Control | |
| After bake and expose: | After development |
| 5.15 μm | 3.96 μm (77.0 percent) |
| After cure | After cure |
| 5.59 μm | 3.925 μm (70.2 percent) |

EXAMPLE 21 n-Butyl n-Butyrate as a Developing Solvent 0.168 Grams of 1,2-dihydro 2,2,4-trimethylquinoline (PDTQ) is added to 33.281 grams of a 50 percent solids DVS bis BCB resin (molecular weight of Mn=4,500 g/mole; Mw=59,000 g/mole) solution in mesitylene and dissolved with heating at 60° C. in a water bath shaker for 30 minutes. The solution is then filtered through a 5.0 micron filter into a clean amber bottle. 0.463 Grams of BAC-M is added to the 30.099 grams of the filtered solution and dissolved with heating at 60° C. in a water bath shaker for 30 minutes.

A clean silicon wafer is spin-coated with a 0.5 percent aqueous solution of 3-aminopropyltriethoxysilane adhesion promoter at a spin speed of 3,500 rpm for 30 seconds. The BAC-M solution is then spin-coated on the wafer using a 10 second spread cycle of 500 rpm followed by a spin speed of 3,500 rpm for 30 seconds to yield a 6.690 micron thick film. The wafer is placed in a nitrogen purged oven at 80° C. for 30 minutes. After cooling to room temperature, the wafer is placed in an Oriel mask aligner and the photodefinable DVS bis BCB film on the wafer is then given an exposure dose of 1,000 mJ/cm$^2$ of light, measured at the 365 nm wavelength, (broad band source 350 to 450 nm) through a quartz photomask. The film thickness is measured with a profilometer to be 6.690 microns. The wafer is then immersed in butyl butyrate for 60 seconds and sprayed dry with a nitrogen stream. The wafer is placed in a nitrogen purged oven at 80° C. for 10 minutes to further dry. After solvent development and drying, the film thickness is 5.105 microns as measured by a profilometer. The film is cured according to the following cure schedule:

50° C. for 5 minutes
50° C. to 100° C. over 5 minutes
100° C. for 15 minutes
100° C. to 150° C. over 15 minutes
150° C. for 15 minutes
150° C. to 250° C. over 60 minutes
250° C. for 60 minutes
250° C. to 100° C. over 120 minutes The film thickness after cure is 5.170 microns as determined by a profilometer.

EXAMPLE 22

Fabrication of a Multiple Layer Structure Consisting of Two Alternating Aluminum and Photodefinable DVS bis BCB Layers 1.006 Grams of PDTQ is added to 199.358 grams of a 50 percent solids DVS bis BCB resin (molecular weight of Mn=4,500 g/mole; Mw=59,000 g/mole) solution in mesitylene and dissolved with heating at 60° C. in a water bath shaker for 1 hour. 3.085 g of BAC-M is added to the solution and dissolved with heating at 60° C. in a water bath shaker for 30 minutes. The solution is then filtered through a 0.5 micron filter into a clean 200 mL amber bottle.

A clean silicon wafer with a thermal silicon oxide layer is sputter-coated with aluminum metal under typical metal deposition process conditions using a Leybold 560 Box Coater. The aluminum is deposited using a DC Magnetron sputtering in argon at 1500 watts for 60 minutes to yield a metal film of approximately 2.0 microns thick. The aluminum is patterned using Shipley Microposit S1400-37 positive photoresist. The Microposit S1400-37 photoresist is deposited on top of the aluminum by spin-coating using a 3 second spread cycle at 500 rpm followed by a 30 second spin cycle at 2,500 rpm which produced a film thickness of approximately 4.0 microns. The photoresist is placed in a nitrogen purged oven at 100° C. for 30 minutes. The wafer is then cooled to room temperature and then placed in a Canon PLA-501FA Mask Aligner which has a medium pressure Hg lamp as a light source. A photomask is placed on top of the wafer and the photoresist is exposed to the light at 405 nm wavelength for an exposure dose of 47 mJ/cm$^2$ The exposed positive photoresist is developed using Shipley Microposit 454 Developer (2 percent KOH). The development is done by immersing the substrates in a filtered, circulated developer bath at 18° C. for 90 seconds. The patterned film is then dump-rinsed in DI-water and spin-dried. The wafer is then flood exposed using the mask aligner light source for 236 mJ/cm$^2$ at the 405 nm wavelength. The wafer is placed in a nitrogen purged oven at 120° C. for 30 minutes. The aluminum metal layer is etched by placing the wafer in an acid bath (48 percent DI-water, 43 percent phosphoric acid, 4.0 percent acetic acid, and 5.4 percent nitric acid) at 45° C. for 15 minutes. The water is then dump-rinsed in DI-water and spin-rinsed-dried to remove residual acid. The photoresist is stripped off of the substrate by placing the wafer on the spin coater and dynamically rinsing it with acetone, followed by methanol; the wafer is then spun until it is dry.

The clean wafer with patterned aluminum metal deposited on top of the thermal silicon oxide, is spin-coated with a 0.5 percent aqueous solution of 3-aminopropyltriethoxysilane adhesion promoter at a spin speed of 2,500 rpm for 30 seconds. The photodefinable solution is then spin-coated using a 10 second spread cycle of 500 rpm followed by a spin speed of 3,500 rpm for 30 seconds to yield a 6.7 micron thick film. The wafer is placed in a nitrogen purged oven at 80° C. for 30 minutes. After cooling to room temperature, the wafer is placed in an Oriel mask aligner and the aluminum pattern on the wafer is aligned to the photomask.

The photodefinable DVS bis BCB film on the wafer is then given an exposure dose of 700 mJ/cm$^2$ of light measured at the 365 nm wavelength (broad band source 350 to 450 nm). The exposed film is developed by immersion into 2-methoxyethyl ether for 90 seconds and sprayed dry with a nitrogen stream. The wafer is "softcured" at 210° C. in a nitrogen purged oven under the following conditions:

50° C. for 5 minutes
50° C. to 100° C. over 5 minutes
100° C. for 15 minutes
100° C. to 150° C. over 15 minutes
150° C. for 15 minutes
150° C. to 210° C. over 30 minutes
210° C. for 30 minutes
210° C. to 100° C. over 120 minutes The wafer is then oxygen plasma cleaned for 15 minutes, dump-rinsed in DI-water, and spin-rinsed dried.

A second 2.0 micron thick aluminum layer is deposited on top of patterned photodefinable DVS bis BCB film and patterned using the same processing conditions as the first metal deposition and patterning. The wafer is then oxygen-plasma-cleaned for 15 minutes, dump-rinsed in DI-water, and spin-rinsed dried.

The wafer is spin-coated with a 0.5 percent aqueous solution of 3-aminopropyltriethoxysilane adhesion promoter at a spin speed of 2,500 rpm for 30 seconds. A second photodefinable DVS bis BCB layer is spin-coated on the second patterned aluminum layer at a spin speed of 3,500 rpm to give a film coating thickness of 6.7 microns. The wafer is placed in a nitrogen purged oven at 80° C. for 30 minutes. After cooling to room temperature, the wafer is placed in an Oriel mask aligner and the aluminum pattern on the wafer is aligned to the photomask. The second photodefinable film is given an exposure dose of 700 mJ/cm$^2$ measured at the 365 nm wavelength (broad band source 350 to 450 nm). The wafer is then immersed in 2-methoxyethyl ether for 90 seconds and sprayed dry with a nitrogen stream. The wafer is placed in a nitrogen purged oven at 80° C. for 10 minutes to further dry. The film on the wafer is cured according to the following cure schedule:

50° C. for 5 minutes
50° C. to 100° C. over 5 minutes
100° C. for 15 minutes
100° C. to 150° C. over 15 minutes
150° C. for 15 minutes
150° C. to 250° C. over 60 minutes
250° C. for 60 minutes
250° C. to 100° C. over 120 minutes The final multilayered structure is of high quality with good adhesion between the polymer and aluminum layers.

EXAMPLES 23–49

Partial Polymerization in a Solvent

A three-necked flask is provided with an agitator, a reflux condenser, thermocouples attached to a temperature controller and a heating mantle operatively connected to the temperature controller. The DVS bis BCB monomer made by the method set out hereinbefore and mesitylene are added to the flask in the proportions stated wherein percent DVS bis BCB monomer is the initial weight percent DVS bis BCB monomer in the total solution.

The agitator is started. The flask is purged with nitrogen and a pad of nitrogen is maintained over the reaction throughout its course. The reaction vessel is then heated to the temperature stated for the time stated. When the reaction is completed, the reactants are either concentrated to 42 percent DVS bis BCB resin in a rotary evaporator at approximately 90° C. and approximately 50 mm Hg pressure or diluted to 42 percent DVS bis BCB resin with additional mesitylene.

Additional samples are polymerized to different Mw at given initial monomer concentrations.

The DVS bis BCB resin solution is then diluted to achieve a viscosity of 300 cps, for example. For obtaining thicker films, such as 20 microns, one may use a solution with a viscosity of 800 cps. The solution is filtered through a 5 micron filter in a class 1000 clean room. Three weight percent, based on the DVS bis BCB resin present, 2,6-di(4-azidobenzylidene), 4-methylcyclohexanone (BAC-M) is added to the solution of DVS bis BCB resin.

Bare silicon wafers are plasma-oxygen-cleaned and dipped in deionized water followed by a spin-rinse dry cycle in a rotating spin dryer. The substrate is then coated with a 0.5 percent aqueous solution of 3-aminopropyltriethoxysilane to promote adhesion. The DVS bis BCB resin solution was then spin-coated onto silicon substrates using approximately 3 mL of solution, a spread cycle of 500 rpm for 10 seconds and a spin cycle of 5000 rpm for 30 seconds. The coated wafers are then prebaked in a nitrogen blanketed oven at 80° C. for 30 minutes. The films on the substrates are exposed to 125 to 1000 mJ/cm$^2$ of 350 to 450 nm wavelength light through a quartz photomask in the hard contact mode using an Oriel mask aligner.

The latent image is developed using a development solvent which washes away the unexposed portions of the film. Typical solvents are 2-methoxyethyl ether (diglyme), n-butyl n-butyrate, Proglyde™ DMM, dipropylene glycol dimethyl ether, or Stoddard solvent. For Examples 30, 32, 33, 37–40, and 42–46, the development solvent is 2-methoxyethyl ether, diglyme. For Examples 31, 34, 36, 41 and 47 the development solvent is n-butyl n-butyrate.

The solvent may be puddled on the coated and exposed substrate followed by spraying additional solvent onto the substrate while spinning at 500 rpm for 30 seconds. Immediately after solvent application is stopped, the spin-speed is increased to 4000 to 5000 rpm for 30 seconds to dry the solvent off. Preferably, diglyme and Proglyde™ DMM solvent are puddled and then spun off. Preferably, n-butyl n-butyrate is sprayed on during spinning.

The thickness of the films is determined by stylus profilometry. The films are cured by heating them in nitrogen at 250° C. for 1 hour. The thickness of the film is again determined and the ratio of the thickness after hard cure to the thickness prior to solvent development is expressed as percent film retention. Physical changes in the film are also noted. If the film fails as by cracking or crazing, the experiment is terminated. Results are shown in Table 13.

TABLE 13

| | Initial % Monomer | Mn × 10³ | Mw × 10³ | Weight % Monomer | Weight % Dimer | Percent Film Retention |
|---|---|---|---|---|---|---|
| 23* | 5.0 | 6.1 | 38.0 | | | Cracks |
| 24* | 5.0 | 8.1 | 60.0 | | | Cracks |
| 25* | 5.0 | 9.2 | 88.0 | | | Cracks |
| 26* | 10.0 | 5.9 | 137.0 | 1.7 | 1.9 | Cracks |
| 27* | 10.0 | 5.6 | 102.0 | | | Cracks |
| 28* | 10.0 | 5.1 | 79.0 | | | Cracks |
| 29* | 10.0 | 4.6 | 59.0 | | | Cracks |
| 30 | 12.0 | 3.9 | 57.0 | 3.3 | 2.6 | 76–81 |
| 31 | 12.0 | 4.6 | 108.0 | 2.7 | 2.2 | 74–79 |
| 32 | 15.0 | 3.2 | 53.0 | 4.2 | 3.6 | 57–69 |
| 33 | 15.0 | 3.7 | 97.0 | 3.5 | 3.1 | 77–82 |
| 34 | 15.0 | 3.9 | 109.0 | 3.3 | 3.1 | 72–78 |
| 35 | 15.0 | 4.0 | 144.0 | 3.2 | 2.8 | 78–82 |
| 36 | 15.0 | 4.0 | 197.0 | | | 76–86 |
| 37 | 20.0 | 2.8 | 68.0 | 4.6 | 4.4 | 66–72 |
| 38 | 20.0 | 3.0 | 90.0 | 4.5 | 4.2 | 72–78 |
| 39 | 20.0 | 3.3 | 140.0 | 4.0 | 3.8 | 74–79 |
| 40 | 20.0 | 3.3 | 170.0 | 4.1 | 3.9 | 76–83 |
| 41 | 25.0 | 2.1 | 188.0 | | | 68–74** |
| 42 | 25.0 | 2.7 | 120.0 | 4.9 | 5.2 | 69–75 |
| 43 | 25.0 | 2.6 | 89.0 | 5.1 | 5.4 | 67–76 |
| 44 | 25.0 | 2.1 | 25.0 | | | 45 |
| 45 | 32.0 | 2.2 | 88.0 | 6.0 | 6.7 | 58–66 |
| 46 | 32.0 | 2.2 | 117.0 | 6.3 | 7.2 | 61–70 |
| 47 | 40.0 | 2.0 | 153.0 | | | 60–65 |
| 48 | 100.0 | 1.3 | 25.0 | 12.0 | 9.0 | 40–50 |
| 49 | *** | 4.8 | 95.0 | 1.2 | 2.1 | 85–95 |

*Not an example of the invention
**Poor Film Quality
***Solvent Precipitated Resin This data in Table 13 indicates that a higher Mw generally gives a higher film retention for the 15, 20, and 25 percent initial monomer concentration. It also shows that outside the range of 12 to 32 percent initial monomer concentration yields crazing on the low end and poorer film retention on the high end. Resins made with 5 percent initial monomer concentration craze upon evaporation of the solvent after spin coating. Resins made with 10 percent initial monomer concentration craze upon cooling down from softbake.

Thinner films are less prone to crazing. Three to 5 micron films may not crack, even at 12 percent initial monomer concentrations. Films thicker than 10 microns may craze even with 18 percent initial monomer concentration after hot plate baking at 120° C. for 1 minute.

EXAMPLES 30–32

Forming a Pattern in a Photodefineable DVS bis BCB Resin Formulation

The exemplified DVS bis BCB monomer is B-staged at 25 weight percent solids in mesitylene for 46 hours at 165° C. and for sufficient time at 145° C. to obtain a viscosity of 4.4 cp at 145° C. (35 cSt at 25° C.) which should be equivalent to an Mw of 140,000 plus or minus 10,000. The DVS bis BCB resin is concentrated by vacuum stripping to 52 weight percent solids (viscosity 4000 cp at 25° C.). The DVS bis BCB resin is formulated by adding the stated amount of BAC-M, the stated amount of 3,3'-diazidophenyl sulfone and the stated amount of AgeRite MA antioxidant. The solutions are agitated for 2 hours on a vortex shaker, overnight on an Eberbach shaker and sonicated for 10 minutes to dissolve the additives and remove any air bubbles.

A clean silicon wafer is spin-coated with a 0.5 percent aqueous solution of 3-aminopropyltriethoxysilane adhesion promoter at a spin speed of 3,000 rpm for 30 seconds. The photodefineable DVS bis BCB resin formulation is spin-coated on the wafer with a 10 second spread cycle at 500 rpm followed by a 2750 rpm spin for 30 seconds. The wafer is prebaked at 80° C. for 20 minutes. The wafer is placed in a Canon mask aligner and exposed through a quartz photomask for 1,000 mJ/cm$^2$ of light measured at 365 nm using a broad band source of 350–450 nm.

After exposure the films are developed by puddling Stoddard's solvent on the surface of the film while the wafer rests on the vacuum chuck of a Solitec model 5110-ND spray developer. After non photo-cured resin visibly dissolves the wafers are spun at 500 rpm for 10 seconds while a stream of Stoddard's solvent is directed at the surface. The wafer is spun at 4,000 rpm for 30 seconds to dry. The wafers are post-baked for 10 minutes at 80° C. under N$_2$ to remove residual solvent. The wafer is heated under N$_2$ at 50° C. for 5 minutes, ramped to 100° C. over 5 minutes, heated at 100° C. for 15 minutes, ramped to 150° C. over 15 minutes, heated at 150° C. for 15 minutes, ramped to 250° C. over 60 minutes, heated at 250° C. for 60 minutes and ramped to 100° C. over 120 minutes.

The film thickness is measured after the prebake and after the hard cure. The ratio of the film thickness after hard cure to the thickness after prebake is the film retention, expressed as a percentage. The results are set out in Table 14.

Example 30 (5 micron formulation) is formulated with 3.0 weight percent BAC-M and 1.0 weight percent AgeRite MA. Example 31 (10 micron formulation) is formulated with 2.0 weight percent BAC-M, 0.75 weight percent 3,3'-diazidophenyl sulfone and 0.75 to 1.0 weight percent AgeRite MA. Example 32 (20 micron formulation) is formulated with 1.0 weight percent BAC-M, 0.9 weight percent 3,3'-diazidophenyl sulfone and 1.0 weight percent AgeRite MA.

TABLE 14

| Example | Prebake Film Thickness (microns) | Post Cure Film Thickness (microns) | Film Retention % |
|---------|----------------------------------|------------------------------------|------------------|
| 30 | 8.43 | 7.38 | 87.5 |
| 31 | 12.18 | 10.10 | 82.9 |
| 32 | 22.8 | 18.9 | 82.8 |

Fifty micron vias were opened and clear with each of these formulations. Twenty-five micron vias were opened and clear in the 10 micron and 5 micron thick films.

EXAMPLES 33–41

Forming a Pattern in a Photodefineable DVS bis BCB Resin Formulation

In the same manner as in Examples 30–32, a pattern is formed and cured. The DVS bis BCB resins are formulated by addition of the stated amount of bis azide. Results are reported in Table 15, wherein ISO is 2,2-bis[4-(4-azidophenoxy)phenyl]propane, the ETHER is 4,4'-diazidophenyl ether and the SULF is 4,4'-diazidophenyl sulfide.

TABLE 15

| Example | Bis Azide wt % | Prebake Film Thickness (microns) | Post Cure Film Thickness (microns) | Film Retention % |
|---------|----------------|----------------------------------|------------------------------------|------------------|
| 33 | 3.0 SULF | 11.81 | 10.10 | 85.09 |
| 34 | 5.5 SULF | 11.64 | 11.21 | 96.3 |
| 35 | 8.0 SULF | 11.54 | 11.41 | 98.9 |
| 36 | 3.0 ISO | 12.63 | 8.55 | 67.7 |
| 37 | 5.5 ISO | 12.63 | 9.81 | 77.6 |
| 38 | 8.0 ISO | 12.65 | 10.68 | 84.43 |
| 39 | 3.0 ETHER | 12.16 | 9.65 | 79.3 |
| 40 | 5.5 ETHER | 12.07 | 10.61 | 87.9 |
| 41 | 8.0 ETHER | 12.15 | 11.10 | 91.4 |

What is claimed is:

1. A mesitylene soluble oligomerized cyclobutarene containing 80 percent or more of oligomers of a degree of polymerization of three or more as determined from peak area percent by GPC, using a refractive index detector, uncorrected for response factors and as measured against polystyrene standards.

2. The oligomerized cyclobutarene of claim 1 wherein the cyclobutarene is divinyltetramethyldisiloxane bisbenzocyclobutane.

3. The oligomerized cyclobutarene of claim 2 containing 90 percent or more of oligomers of a degree of polymerization of three or more.

4. A mesitylene soluble oligomerized cyclobutarene containing 80 percent or more of oligomers of a molecular weight of 1,000 or more as determined from peak area percent by GPC, using a refractive index detector, uncorrected for response factors and as measured against polystyrene standards.

5. The oligomerized cyclobutarene of claim 4 wherein the cyclobutarene is divinyltetramethyldisiloxane bisbenzocyclobutane.

6. The oligomerized cyclobutarene of claim 5 containing 90 percent or more of oligomers of a molecular weight of 1,000 or more.

7. A mesitylene soluble oligomerized cyclobutarene formed by mixing a starting oligomerized cyclobutarene dissolved in a miscible solvent with a nonsolvent for higher molecular weight species to precipitate out higher molecular weight species and recovering the precipitated higher molecular weight species.

8. The oligomerized cyclobutarene of claim 7 wherein the cyclobutarene is divinyltetramethyldisiloxane bisbenzocyclobutane.

9. The mesitylene soluble oligomerized divinyltetramethyldisiloxane bisbenzocyclobutane of claim 8 wherein at least 80 weight percent of the divinyltetramethyldisiloxane bisbenzocyclobutane monomer is removed from the starting oligomerized divinyltetramethyldisiloxane bisbenzocyclobutane.

10. The mesitylene soluble oligomerized divinyltetramethyldisiloxane bisbenzocyclobutane of claim 9 wherein at least 90 weight percent of the divinyltetramethyldisiloxane bisbenzocyclobutane monomer is removed from the starting oligomerized divinyltetramethyldisiloxane bisbenzocyclobutane.

* * * * *